US012702673B2

(12) United States Patent
Muñoz et al.

(10) Patent No.: US 12,702,673 B2
(45) Date of Patent: *Aug. 11, 2026

(54) SULFATED C19 STEROID HORMONES TO TREAT AND/OR PREVENT PROTEOTOXICITY IN PROTEIN-AGGREGATION DISEASES

(71) Applicant: UNIVERSIDAD PABLO DE OLAVIDE, Seville (ES)

(72) Inventors: Manuel J. Muñoz, Seville (ES); Mercedes M. Pérez-Jiménez, Seville (ES); Ángel M. Carrión, Seville (ES)

(73) Assignee: UNIVERSIDAD PABLO DE OLAVIDE, Seville (ES)

( * ) Notice: Subject to any disclaimer, the term of this patent is extended or adjusted under 35 U.S.C. 154(b) by 466 days.

This patent is subject to a terminal disclaimer.

(21) Appl. No.: 18/250,687

(22) PCT Filed: Oct. 26, 2021

(86) PCT No.: PCT/EP2021/079710

§ 371 (c)(1),
(2) Date: Apr. 26, 2023

(87) PCT Pub. No.: WO2022/090247

PCT Pub. Date: May 5, 2022

(65) Prior Publication Data

US 2023/0405020 A1 Dec. 21, 2023

(30) Foreign Application Priority Data

Oct. 26, 2020 (EP) .................................... 20382931

(51) Int. Cl.
*A61K 31/568* (2006.01)
*A61K 31/366* (2006.01)
(Continued)

(52) U.S. Cl.
CPC .......... *A61K 31/568* (2013.01); *A61K 31/366* (2013.01); *A61K 31/5685* (2013.01); *A61P 25/28* (2018.01)

(58) Field of Classification Search
CPC .... A61K 31/366; A61K 31/37; A61K 31/568; A61K 31/5685; A61K 2300/00; A61P 25/16; A61P 25/28
See application file for complete search history.

(56) References Cited

U.S. PATENT DOCUMENTS 5,556,847 A 9/1996 Johnson et al.
5,888,996 A * 3/1999 Farb ....................... A61K 31/57 514/182

FOREIGN PATENT DOCUMENTS

WO 2015161078 A1 10/2015
WO 2019243453 A1 12/2019

OTHER PUBLICATIONS

Trigo et al., Unravelling protein aggregation as an ageing related process or a neuropathological response, Ageing Research Reviews, vol. 51, 67-77, Feb. 11, 2019 (Year: 2019).*

(Continued)

*Primary Examiner* — Sarah Pihonak
*Assistant Examiner* — Padmaja S Rao
(74) *Attorney, Agent, or Firm* — Seed Intellectual Property Law Group LLP

(57) ABSTRACT

The present invention is encompassed within the field of medicine and provides a composition for use in the treatments and/or prevention of protein-aggregation diseases.

14 Claims, 15 Drawing Sheets

Specification includes a Sequence Listing.

(51) Int. Cl.
*A61K 31/5685* (2006.01)
*A61P 25/28* (2006.01)

(56) References Cited

OTHER PUBLICATIONS

Perez-Jimenez et al., Steroid hormones sulfatase inactivation extends lifespan and ameliorates age-related diseases, bioRxiv preprint, Feb. 6, 2019 (Year: 2019).*
Bianchi et al., "Androgen Therapy in Neurodegenerative Diseases," Journal of the Endocrine Society 4(11):1-18, Aug. 21, 2020. (18 pages).
Eisenberg et al., "The Amyloid State of Proteins in Human Diseases," Cell 148(6):1188-1203, Mar. 16, 2012. (16 pages).
Gouras et al., "Testosterone reduces neuronal secretion of Alzheimer's β-amyloid peptides," PNAS 97(3):1202-1205, Feb. 2000. (4 pages).
Hoffner et al., "Monomeric, Oligomeric and Polymeric Proteins in Huntington Disease and Other Diseases of Polyglutamine Expansion," Brain Sci. 4(1):91-122, Mar. 3, 2014. (32 pages).
Jack Jr. et al., "Hypothetical model of dynamic biomarkers of the Alzheimer's pathological cascade," Lancet Neurol. 9:119-128, Jan. 2010. (10 pages).
Li et al., "Illumina Synthetic Long Read Sequencing Allows Recovery of Missing Sequences even in the "Finished" C. elegans Genome," Scientific Reports 5(10814):1-15, Jun. 3, 2015. (15 pages).
Okun et al., "Beneficial Effects of Testosterone Replacement for the Nonmotor Symptoms of Parkinson Disease," Arch. Neurol. 59:1750-1753, Nov. 2002. (4 pages).
Pérez-Jiménez et al., "Steroid hormones sulfatase inactivation extends lifespan and ameliorates age-related diseases", bioRxiv, doi:10.1101/541730, Feb. 6, 2019. (26 pages).
Pérez-Jiménez et al., "Steroid hormones sulfatase inactivation extends lifespan and ameliorates age-related diseases," Nature Communications 12(49):1-12, Jan. 4, 2021. (12 pages).
Purohit et al., "Steroid sulfatase inhibitors for estrogen- and androgen-dependent cancers," J. Endocrinol. 212:99-110, Aug. 22, 2011. (12 pages).
Sipe et al., "Amyloid fibril protein nomenclature: 2012 recommendations from the Nomenclature Committee of the International Society of Amyloidosis," Amyloid 19(4):167-170, 2012. (4 pages).

* cited by examiner a b c d a b

Alzheimer model treated with AS (Androsterone Sulfate)

Strain: GMC101

Phenotype: Paralysis 5 biological replicates
N>200 worms
X-square 2-sided (total n):
* ≤ 0.05
**≤ 0.01

SEQUENCE LISTING

```
<160> NUMBER OF SEQ ID NOS: 19

<210> SEQ ID NO 1
<211> LENGTH: 60
<212> TYPE: PRT
<213> ORGANISM: Artificial Sequence
<220> FEATURE:
<223> OTHER INFORMATION: Fig. 6 Sequence SUL-2

<400> SEQUENCE: 1

Pro Asn Ile Val Ile Leu Met Ile Asp Asp Leu Gly Tyr Gly Asp Ile
1               5                   10                  15

Ala Ser Tyr Gly His Pro Thr Gln Glu Tyr Thr Gln Val Asp Arg Met
            20                  25                  30

Ala Ala Glu Gly Thr Arg Phe Thr Gln Ala Tyr Ser Ala Asp Ser Met
        35                  40                  45
```

-continued

```
Cys Ser Pro Ser Arg Ala Gly Phe Ile Thr Gly Arg
    50                  55                  60


<210> SEQ ID NO 2
<211> LENGTH: 60
<212> TYPE: PRT
<213> ORGANISM: Artificial Sequence
<220> FEATURE:
<223> OTHER INFORMATION: Fig. 6 Sequence ARSC

<400> SEQUENCE: 2

Pro Asn Ile Ile Leu Val Met Ala Asp Asp Leu Gly Ile Gly Asp Pro
1               5                   10                  15

Gly Cys Tyr Gly Asn Lys Thr Ile Arg Thr Pro Asn Ile Asp Arg Leu
            20                  25                  30

Ala Ser Gly Gly Val Lys Leu Thr Gln His Leu Ala Ala Ser Pro Leu
        35                  40                  45

Cys Thr Pro Ser Arg Ala Ala Phe Met Thr Gly Arg
    50                  55                  60


<210> SEQ ID NO 3
<211> LENGTH: 60
<212> TYPE: PRT
<213> ORGANISM: Artificial Sequence
<220> FEATURE:
<223> OTHER INFORMATION: Fig. 6 Sequence ARSD

<400> SEQUENCE: 3

Pro Asn Ile Leu Leu Ile Met Ala Asp Asp Leu Gly Thr Gly Asp Leu
1               5                   10                  15

Gly Cys Tyr Gly Asn Asn Thr Leu Arg Thr Pro Asn Ile Asp Gln Leu
            20                  25                  30

Ala Glu Glu Gly Val Arg Leu Thr Gln His Leu Ala Ala Ala Pro Leu
        35                  40                  45

Cys Thr Pro Ser Arg Ala Ala Phe Leu Thr Gly Arg
    50                  55                  60


<210> SEQ ID NO 4
<211> LENGTH: 59
<212> TYPE: PRT
<213> ORGANISM: Artificial Sequence
<220> FEATURE:
<223> OTHER INFORMATION: Fig. 6 Sequence ARSE

<400> SEQUENCE: 4

Pro Asn Ile Leu Leu Leu Met Ala Asp Asp Leu Gly Ile Gly Asp Ile
1               5                   10                  15

Gly Cys Tyr Gly Asn Asn Thr Met Arg Thr Pro Asn Ile Arg Leu Ala
            20                  25                  30

Glu Asp Gly Val Lys Leu Thr Gln His Ile Ser Ala Ala Ser Leu Cys
        35                  40                  45

Thr Pro Ser Arg Ala Ala Phe Leu Thr Gly Arg
    50                  55


<210> SEQ ID NO 5
<211> LENGTH: 60
<212> TYPE: PRT
<213> ORGANISM: Artificial Sequence
<220> FEATURE:
<223> OTHER INFORMATION: Fig. 6 Sequence ARSH

<400> SEQUENCE: 5
```

```
Pro Asn Ile Val Leu Leu Met Ala Asp Asp Leu Gly Val Gly Asp Leu
1               5                   10                  15

Cys Cys Tyr Gly Asn Asn Ser Val Ser Thr Pro Asn Ile Asp Arg Leu
            20                  25                  30

Ala Ser Glu Gly Val Arg Leu Thr Gln His Leu Ala Ala Ala Ser Met
        35                  40                  45

Cys Thr Pro Ser Arg Ala Ala Phe Leu Thr Gly Arg
    50                  55                  60


<210> SEQ ID NO 6
<211> LENGTH: 60
<212> TYPE: PRT
<213> ORGANISM: Artificial Sequence
<220> FEATURE:
<223> OTHER INFORMATION: Fig. 6 Sequence ARSF

<400> SEQUENCE: 6

Pro Asn Ile Val Leu Ile Met Val Asp Asp Leu Gly Ile Gly Asp Leu
1               5                   10                  15

Gly Cys Tyr Gly Asn Asp Thr Met Arg Thr Pro His Ile Asp Arg Leu
            20                  25                  30

Ala Arg Glu Gly Val Arg Leu Thr Gln His Ile Ser Ala Ala Ser Leu
        35                  40                  45

Cys Ser Pro Ser Arg Ser Ala Phe Leu Thr Gly Arg
    50                  55                  60


<210> SEQ ID NO 7
<211> LENGTH: 60
<212> TYPE: PRT
<213> ORGANISM: Artificial Sequence
<220> FEATURE:
<223> OTHER INFORMATION: Fig. 6 Sequence ARSG

<400> SEQUENCE: 7

Pro Asn Phe Val Ile Ile Leu Ala Asp Asp Met Gly Trp Gly Asp Leu
1               5                   10                  15

Gly Ala Asn Trp Ala Glu Thr Lys Asp Thr Ala Asn Leu Asp Lys Met
            20                  25                  30

Ala Ser Glu Gly Met Arg Phe Val Asp Phe His Ala Ala Ala Ser Thr
        35                  40                  45

Cys Ser Pro Ser Arg Ala Ser Leu Leu Thr Gly Arg
    50                  55                  60


<210> SEQ ID NO 8
<211> LENGTH: 60
<212> TYPE: PRT
<213> ORGANISM: Artificial Sequence
<220> FEATURE:
<223> OTHER INFORMATION: Fig. 6 Sequence ARSA

<400> SEQUENCE: 8

Pro Asn Ile Val Leu Ile Phe Ala Asp Asp Leu Gly Tyr Gly Asp Leu
1               5                   10                  15

Gly Cys Tyr Gly His Pro Ser Ser Thr Thr Pro Asn Leu Asp Gln Leu
            20                  25                  30

Ala Ala Gly Gly Leu Arg Phe Thr Asp Phe Tyr Val Pro Val Ser Leu
        35                  40                  45

Cys Thr Pro Ser Arg Ala Ala Leu Leu Thr Gly Arg
    50                  55                  60
```

-continued

```
<210> SEQ ID NO 9
<211> LENGTH: 11
<212> TYPE: PRT
<213> ORGANISM: Artificial Sequence
<220> FEATURE:
<223> OTHER INFORMATION: Fig. 6 Sequence SUL-2_wormbase

<400> SEQUENCE: 9

Ser Lys Arg Phe Arg Gly Ser Ser Lys Glu Ala
1               5                   10


<210> SEQ ID NO 10
<211> LENGTH: 117
<212> TYPE: PRT
<213> ORGANISM: Artificial Sequence
<220> FEATURE:
<223> OTHER INFORMATION: Fig. 6 Sequence SUL-2_modified

<400> SEQUENCE: 10

Ser Lys Arg Phe Arg Gly Ser Ser Ile Tyr Gly Asp Ser Ile Asn Glu
1               5                   10                  15

Met Ser Trp Ala Val Gly Glu Val Leu Asp Ser Leu Val Asn Ala Gly
            20                  25                  30

Ile Ala Glu Asn Thr Leu Val Ile Leu Met Ser Asp His Gly Pro His
        35                  40                  45

Val Glu Leu Cys Leu Asn Gly Gly Ser Thr Ala Gly Leu Lys Gly Gly
    50                  55                  60

Lys Ser Asn Ser Tyr Glu Gly Gly Phe Arg Ile Pro Phe Ile Ala Trp
65                  70                  75                  80

Gln Pro Gly Thr Val Lys Pro Ser Arg Val Ser His Glu Val Ile Ser
                85                  90                  95

Ser Met Asp Leu Phe Pro Thr Phe Arg Gly Met Gln Glu Gln Cys Leu
            100                 105                 110

Phe Glu Lys Glu Ala
        115


<210> SEQ ID NO 11
<211> LENGTH: 120
<212> TYPE: PRT
<213> ORGANISM: Artificial Sequence
<220> FEATURE:
<223> OTHER INFORMATION: Fig. 6 Sequence SUL-2_curated

<400> SEQUENCE: 11

Ser Lys Arg Phe Arg Gly Ser Ser Val Arg Gly Ile Tyr Gly Asp Ser
1               5                   10                  15

Ile Asn Glu Met Ser Trp Ala Val Gly Glu Val Leu Asp Ser Leu Val
            20                  25                  30

Asn Ala Gly Ile Ala Glu Asn Thr Leu Val Ile Leu Met Ser Asp His
        35                  40                  45

Gly Pro His Val Glu Leu Cys Leu Asn Gly Gly Ser Thr Ala Gly Leu
    50                  55                  60

Lys Gly Gly Lys Ser Asn Ser Tyr Glu Gly Gly Phe Arg Ile Pro Phe
65                  70                  75                  80

Ile Ala Trp Gln Pro Gly Thr Val Lys Pro Ser Arg Val Ser His Glu
                85                  90                  95

Val Ile Ser Ser Met Asp Leu Phe Pro Thr Phe Arg Gly Met Gln Glu
            100                 105                 110

Gln Cys Leu Phe Glu Lys Glu Ala
```

-continued

```
        115                 120


<210> SEQ ID NO 12
<211> LENGTH: 120
<212> TYPE: PRT
<213> ORGANISM: Artificial Sequence
<220> FEATURE:
<223> OTHER INFORMATION: Fig. 6 Sequence CRE-SUL-2

<400> SEQUENCE: 12

Ser Lys Arg Phe Arg Gly Ser Ser Val Arg Gly Ile Tyr Gly Asp Ser
1               5                   10                  15

Ile Asn Glu Met Ser Trp Ala Val Gly Glu Val Leu Asp Ser Leu Val
            20                  25                  30

Asn Ala Gly Ile Ala Glu Asn Thr Leu Val Ile Leu Met Ser Asp His
        35                  40                  45

Gly Pro His Val Glu Leu Cys Leu Asn Gly Gly Ser Thr Ala Gly Leu
    50                  55                  60

Lys Gly Gly Lys Ser Asn Ser Tyr Glu Gly Gly Phe Arg Ile Pro Phe
65                  70                  75                  80

Ile Ala Trp Gln Pro Gly Thr Val Lys Pro Ser Arg Val Ser His Glu
                85                  90                  95

Val Val Ser Ser Met Asp Leu Phe Pro Thr Phe Arg Ala Met Asn Glu
            100                 105                 110

Glu Cys Leu Phe Glu Lys Glu Ala
        115                 120


<210> SEQ ID NO 13
<211> LENGTH: 120
<212> TYPE: PRT
<213> ORGANISM: Artificial Sequence
<220> FEATURE:
<223> OTHER INFORMATION: Fig 6 Sequence CBR-SUL-2

<400> SEQUENCE: 13

Ser Lys Arg Phe Arg Gly Ser Ser Val Arg Gly Ile Tyr Gly Asp Ser
1               5                   10                  15

Ile Asn Glu Met Ser Trp Ala Val Gly Glu Val Leu Asp Ser Leu Val
            20                  25                  30

Asn Ala Gly Ile Ala Glu Asn Thr Leu Val Ile Leu Met Ser Asp His
        35                  40                  45

Gly Pro His Val Glu Leu Cys Leu Asn Gly Gly Ser Thr Ala Gly Leu
    50                  55                  60

Lys Gly Gly Lys Ser Asn Ser Tyr Glu Gly Gly Phe Arg Ile Pro Phe
65                  70                  75                  80

Ile Ala Trp Gln Pro Gly Thr Val Lys Pro Ser Arg Val Ser His Glu
                85                  90                  95

Val Ile Ser Ser Met Asp Leu Phe Pro Thr Phe Arg Ala Met Asn Glu
            100                 105                 110

Glu Cys Leu Phe Glu Lys Glu Ala
        115                 120


<210> SEQ ID NO 14
<211> LENGTH: 8
<212> TYPE: PRT
<213> ORGANISM: Artificial Sequence
<220> FEATURE:
<223> OTHER INFORMATION: Fig. 6 SUL-2 wormbase

<400> SEQUENCE: 14
```

-continued

Ser Lys Arg Phe Arg Gly Ser Ser
1               5

<210> SEQ ID NO 15
<211> LENGTH: 49
<212> TYPE: PRT
<213> ORGANISM: Artificial Sequence
<220> FEATURE:
<223> OTHER INFORMATION: Fig. 6 SUL-2 modified

<400> SEQUENCE: 15

Ile Tyr Gly Asp Ser Ile Asn Glu Met Ser Trp Ala Val Gly Glu Val
1               5                   10                  15

Leu Asp Ser Leu Val Asn Ala Gly Ile Ala Glu Asn Thr Leu Val Ile
            20                  25                  30

Leu Met Ser Asp His Gly Pro His Val Glu Leu Cys Leu Asn Gly Gly
        35                  40                  45

Ser

<210> SEQ ID NO 16
<211> LENGTH: 60
<212> TYPE: PRT
<213> ORGANISM: Artificial Sequence
<220> FEATURE:
<223> OTHER INFORMATION: Fig. 6 SUL-2 curated, CRE-SUL-2, and CBR-SUL-2

<400> SEQUENCE: 16

Ser Lys Arg Phe Arg Gly Ser Ser Val Arg Gly Ile Tyr Gly Asp Ser
1               5                   10                  15

Ile Asn Glu Met Ser Trp Ala Val Gly Glu Val Leu Asp Ser Leu Val
            20                  25                  30

Asn Ala Gly Ile Ala Glu Asn Thr Leu Val Ile Leu Met Ser Asp His
        35                  40                  45

Gly Pro His Val Glu Leu Cys Leu Asn Gly Gly Ser
    50                  55                  60

<210> SEQ ID NO 17
<211> LENGTH: 60
<212> TYPE: PRT
<213> ORGANISM: Artificial Sequence
<220> FEATURE:
<223> OTHER INFORMATION: Fig. 6 SUL-2 modified and curated.

<400> SEQUENCE: 17

Thr Ala Gly Leu Lys Gly Gly Lys Ser Asn Ser Tyr Glu Gly Gly Phe
1               5                   10                  15

Arg Ile Pro Phe Ile Ala Trp Gln Pro Gly Thr Val Lys Pro Ser Arg
            20                  25                  30

Val Ser His Glu Val Ile Ser Ser Met Asp Leu Phe Pro Thr Phe Arg
        35                  40                  45

Gly Met Gln Glu Gln Cys Leu Phe Glu Lys Glu Ala
    50                  55                  60

<210> SEQ ID NO 18
<211> LENGTH: 60
<212> TYPE: PRT
<213> ORGANISM: Artificial Sequence
<220> FEATURE:
<223> OTHER INFORMATION: Fig. 6 CRE-SUL-2

<400> SEQUENCE: 18

-continued

```
Thr Ala Gly Leu Lys Gly Gly Lys Ser Asn Ser Tyr Glu Gly Gly Phe
1               5                   10                  15

Arg Ile Pro Phe Ile Ala Trp Gln Pro Gly Thr Val Lys Pro Ser Arg
            20                  25                  30

Val Ser His Glu Val Val Ser Ser Met Asp Leu Phe Pro Thr Phe Arg
        35                  40                  45

Ala Met Asn Glu Glu Cys Leu Phe Glu Lys Glu Ala
    50                  55                  60


<210> SEQ ID NO 19
<211> LENGTH: 60
<212> TYPE: PRT
<213> ORGANISM: Artificial Sequence
<220> FEATURE:
<223> OTHER INFORMATION: Fig. 6 CBR-SUL-2

<400> SEQUENCE: 19

Thr Ala Gly Leu Lys Gly Gly Lys Ser Asn Ser Tyr Glu Gly Gly Phe
1               5                   10                  15

Arg Ile Pro Phe Ile Ala Trp Gln Pro Gly Thr Val Lys Pro Ser Arg
            20                  25                  30

Val Ser His Glu Val Ile Ser Ser Met Asp Leu Phe Pro Thr Phe Arg
        35                  40                  45

Ala Met Asn Glu Glu Cys Leu Phe Glu Lys Glu Ala
    50                  55                  60
```

SULFATED C19 STEROID HORMONES TO TREAT AND/OR PREVENT PROTEOTOXICITY IN PROTEIN-AGGREGATION DISEASES

REFERENCE TO AN ELECTRONIC SEQUENCE LISTING

The contents of the electronic sequence listing (920205-402USPC-SL; Size: 13,368 bytes; and Date of Creation: Jan. 20, 2026) is herein incorporated by reference in its entirety and is being submitted electronically.

TECHNICAL FIELD OF THE INVENTION

The present invention is encompassed within the field of medicine and provides a composition for use in the treatments and/or prevention of protein-aggregation diseases.

BACKGROUND OF THE INVENTION

Animals can extend life span by activating different genetic pathways. This increase of longevity is a regulated process that relay in the coordination of different tissues and environmental signals. Hormones are key players in tissues and cell communication. Consequently, they are involved in different pathways that regulate longevity, among those insulin and insulin-like growth factor, TGFβ or dafachronic acids which are described to affect life span at least in the model organism *Caenorhabditis elegans*. Gonad is an endocrine tissue that produces steroids hormones to regulate different physiological aspects of the organism, including longevity. In *C. elegans*, germline ablation extends life span by non-completely understood mechanisms. Several factors are needed for the increase in longevity, including synthesis of dafachronic acid by the somatic gonad as well as the transcription factor encoded by daf-16, homologue to the human FOXO, and the nuclear receptors encoded genes daf-12, nhr-80 and nhr-492.

The classical function of steroid hormones is considered to be the activation of hormones receptors to transcribe their target genes. Steroid hormones are not only produced in gonads but also in other tissues. Those produced in the nervous system are known as neurosteroids. Neurosteroids, in addition to bind to hormone receptors, modulate neurotransmission either through direct interaction with neurotransmitter receptors or by other mechanisms. Steroid hormones can be sulfated by a sulfotransferase enzyme, generating a profound change in the chemical features of the hormone that impairs its function as hormone receptor activator. Those sulfated hormones are considered to be an inactive reservoir of hormones that can be activated upon removal of the sulfate moiety by the activity of hormone sulfatases. Sulfated steroid hormones can also be active as neurosteroids, regulating neurotransmission.

Some sulfated steroid hormones, like dehydroepiandrosterone sulfate (DHEAS), have long been related to aging. The level of this hormone declines with age and in age-related diseases such as sarcopenia or Alzheimer's disease, which has generated the speculation of a causative effect.

Here we show that inhibition of the steroid sulfatase generates an increase of the percentage of sulfated hormones and, associated with that, an increase in longevity and the improvement of the symptoms related to protein aggregation diseases. This increase in longevity is mainly dependent on the same factors described for longevity caused by germline ablation. Treatment with STX64, a specific inhibitor of the steroid sulfatase enzyme, mimics the beneficial effects in longevity and protein aggregation diseases observed in the mutant. Interestingly, treatment with STX64 also ameliorates the cognitive symptoms and plaque formation in a mammalian model of Alzheimer's disease. Finally, the observed phenotypes are recapitulated by treatment with sulfated C19 androgens steroid hormones but not with the non-sulfated forms or the sulfated C21 pregnenolone hormone, indicating that the causative beneficial effect of sul-2 inhibition is due to the increase of sulfated C19 steroid hormones rather than reduction of the non-sulfated form. This invention thus demonstrates that STX64 or specific sulfated C19 steroid hormones are a possible treatment for aging and/or aging-related diseases, more particularly specific sulfated C19 steroid hormones extend lifespan and protect against aging-associated proteotoxicity.

BRIEF DESCRIPTION OF THE FIGURES

FIG. 1*a* illustrates that sul-2(pv17) point mutation allele lives longer than wild type.

FIG. 1*b* illustrates that the null allele sul-2 (gk187) also increases lifespan.

FIG. 1*c* illustrates phylogenetic tree of mammalian sulfatases and the three *C. elegans* sulfatases. Note that SUL-2 clusters with steroid sulfatases (type C) among others, in blue. Phylogenetic relation with other *C. elegans* sulfatases is indicated in grey.

FIG. 1*d* illustrates that inhibition of steroid hormones sulfatase by STX64 (1 μg/ml) increases lifespan in wild type animals, but not in sul-2 (gk187) background. Worms were cultivated in UV-killed *E. coli.*

FIG. 1*e* illustrates that deletion of sul-2 generates an increase in the percentage of steroid hormones in the sulfated stage. Data from three independent assays are shown. One-tailed Mann-Whitney t-test.

FIG. 2*n* illustrates that sul-2 is transcriptional expressed in sensory neurons, mainly ADF and ASE in the head, and PHA and PHB in the tail. Scale bar 10 μm.

FIG. 3*a* illustrates that NL5901 strain expressing α-synuclein in muscle cells reduce mobility with age at a slower rate in a sul-2(gk187) background (n≥17 per day). Statistic test vs α-synuclein control.

FIG. 3*p* illustrates effect of oral administration with STX64 in more than 15-month-old APP-PS1 mice, and comparation with APP-PS1 and wild type mice older than 15 months in the passive avoidance test. The number of mice in each group were >5. In histological analysis, * represent significant differences between vehicle- and STX64 administrated APP-PS1 mice. In behavioral test, * represent significant differences between the short-term and long-term memory sessions (STM and LTM, respectively) and the training session in the same experimental group; and, + represent significant differences between the STM and LTM sessions between each experimental group and β-amyloid group. A symbol, p<0.05, two symbols, p<0.01, and three symbols, p<0.001.

FIG. 4*a* illustrates that NL5901 strain expressing α-synuclein in muscle cells reduce mobility with age. Treatment with DHEAS, TS or ES improves the mobility (1 μg/ml). Data from three biological replicates are displayed, n=30.

FIG. 4*b* illustrates that paralysis of GMC101 Alzheimer's disease model is ameliorate with TS and ES. Data from six biological replicates are displayed, n≥200. Additional assays in normal NGM plates are shown in FIG. 13*a*.

FIGS. 4*c* and 4*d* illustrate that no effect is observed with non-sulfated steroid hormone DHEA or testosterone (T), neither with sulfated C21 steroid hormone, pregnenolone sulfate (PregS) in Parkinson's model, NL5901 strain (1 μg/ml). Data from three biological replicates are displayed, n=30.

FIG. 4*e* illustrates that treatment with abiraterone (Abi) (1 μg/ml) does not affect mobility phenotype of NL5901 strain but suppresses the beneficial effect of sul-2 deletion allele. Data from three biological replicates are displayed, n≥30.

FIG. 4*f* illustrates that treatment with ES (1 μg/ml) increases life span in a wild type background but does not further increase in sul-2(gk187).

FIG. 4*g* illustrates that DHEAS or TS (1 μg/ml) does not affect longevity. Additional biological replicates assays are shown in FIGS. 13*c* and *d*.

FIG. 5*a* illustrates that sul-2(pv17) is long lived and fer-15(b26) does not affect their lifespan.

FIG. 5*b* illustrates that sul-2 mutants are long-lived at 20° C.

FIG. 5*c* illustrates that sul-2 mutants are long-lived at 25° C.

FIG. 5*d* illustrates that pumping rate of sul-2 mutants are similar to wild type at adult day 1, while pv17 allele keeps higher pumping rate than wild type at adult day 6 stage. Worms were growth at 16° C. until L4, then shifted to 25° C. considering this Day 0 of adulthood. The pumping was counted under the Leica stereoscope at 100× magnification for 30 seconds. Data display from two independent biological assays (n=30 per day). Two-tailed Mann-Whitney t-test, ***p=0.0006.

FIG. 5*e* illustrates that thrashing in sul-2(gk187) is similar to wild type but is slightly lower in sul-2 (pv17) at 25° C. on day 1 of adulthood. On day 6 at 25° of adulthood, the thrashing on sul-2(gk187) is lower than wild type and sul-(pv17), with no differences among these last strains. The population of sul-2(gk17) at day 6 seems to distribute into two different populations, one with almost no thrashing and other with values similar to wild type a sul-2(pv17). Data displayed from two independent biological assays (n=20 per day).

FIG. 5*f* illustrates that sul-1(gk151) and sul-3(tm6179) do not increase life span.

FIG. 5*g* illustrates that a small percentage of daf-2(e979) animals arrest development in Dauer larvae at 16° C., sul-2(pv17) mutant does not show any larval arrest but enhances dauer arrest of daf-2(e979).

FIG. 5*h* illustrates that most daf-2(e1370) animals arrest in Dauer stage when develop at 25° C., but small percentage arrest in L1 stage. In this condition, all animals from daf-2(e1370); sul-2(pv17) double mutants arrest at L1 stage. Similarly, more than 50% of animals arrest in L1 stage in daf-2(m577); sul-2(pv17) background, while none of the single mutants show this phenotype.

FIG. 5*i* illustrates example of sul-2(pv17) larvae, Dauer larval arrest of daf-2(e1370) or L1 arrest of daf-2(e1370); sul-2(pv17) and daf-2(e1370); sul-2(gk187) at 25° C. Animals were grown up to L4 at 16° C., then shifted at 25° C., progeny were scored or imaged after 72 hours. Photographs were taken in a Leica scope.

FIG. 6*a* shows the pv17 allele is a missense mutation that changes the glycine indicated with asterisk to an aspartic acid residue. The mutation is located close to an evolutionary constrained region (ECR), indicated with the bar at the bottom and also near to the catalytic core of sulfatases (in green).

FIG. 6*b* shows the DNA sequence identified in the wild type sul-2 differs to the one published in wormbase (SUL-2_wormbase, SEQ ID NO. 14) and identified as orthologue to ARSA (www.wormbase.org), this sequence misses 459 bp, also described recently by Li et al. (2015) and predicted as part of an new exon [wormbase_170818 gw3] based on RNAseq data (SUL-2_modified, SEQ ID NO. 15). The protein sequence obtained by cDNA sequencing of yk387h10 clone (SUL-2_curated, SEQ ID NO. 16) differs to the one predicted in three amino acids (in bold). Notice that the three amino acids identified in this sequence are present also in other species (CRE: *C. remanei*, CBR: C. brigssae).

FIG. 6*c* shows exon intron composition of wild type sul-2 and region deleted in the gk187 allele (in red). The mutant lesion is available at wormbase (www.worm-base.org). This allele deletes the sequence that encodes to the catalytic core of sulfatases (in green) and generates a frame shift, conserving only the four first amino acids of the original sequence; therefore, we consider gk187 a null allele. The pv17 allele location is indicated with asterisk, the new DNA fragment identified in yellow and the new exon in purple.

FIG. 7*a* illustrates that STX64 in non-UV *E. coli* increases lifespan of wild type.

FIGS. 7*b* and 7*c* illustrate that Dosis curves of STX64 in non-UV *E. coli* show a significant effect at 1 μg/ml and 5 μg/ml.

FIG. 7*d* shows photographs of wild type and daf-2(e1370) at 25° C. DMSO (STX64 vehicle) does not affect development of wild type, neither STX64 treatment, daf-2(e1370) arrests mostly in Dauer stage at 25° C., but mainly arrests in L1 when treated with STX64, similar interaction is also observed in the sul-2 mutants. Photographs were taken in a Leica scope. Arrow heads: Dauers, arrows: L1s.

FIGS. 8*a* and 8*b* illustrate that sul-2(pv17) enhances longevity of two daf-2 alleles, e1370 and m577.

FIGS. 8*c* and 8*d* illustrate that sul-2(pv17) longevity is suppressed by two alleles of daf-16, mu86 and m26.

FIG. 8*e* illustrates that sul-2(pv17) longevity is suppressed by tcer-1(tm1452).

FIG. 8*f* illustrates that sul-2(pv17) longevity is partially suppressed by nhr-80(tm1011).

FIG. 8*g* illustrates that sul-2(pv17) longevity is not suppressed by nhr-49(nr2041).

FIG. 8*h* illustrates that sul-2(pv17) increases lifespan in glp-1 background.

FIG. 8*i* illustrates that sul-2(pv17) longevity is suppressed by daf-12(m20).

FIG. 9*a* is a series of micrographs showing representative images of Pdaf-16::gfp::daf-16 location in wild type (left panel) and sul-2 mutants (central and right panels). Both sul-2 mutants increase the nuclear location of DAF-16 in intestinal cells, like in germ-line less animals. Scale 20 μm.

FIG. 9*b* illustrates quantifications of nuclear fluorescence in the anterior intestinal cells. Data from two independent assays, n≥34 nuclei per condition. One-way ANOVA test.

FIG. 9*c* illustrates that sul-2 mutants have similar brood size to control at 20° C. One-way ANOVA test; ns.

FIG. 9*d* illustrates that the reproductive period of sul-2 mutants are not affected at 20° C.

FIG. 9*e* illustrates that sul-2 mutants show normal gonad morphology. Micrographs of one representative gonadal arm in late L4 for each strain are shown.

FIG. 10*a* shows that transcriptional reporter for sul-2 is expressed in sensory neurons. Imaged in fluorescence and merged with the bright field.

FIG. 10*b* shows representative images of sul-2 extrachromosomal expression in amphids, most transgenic animals express sul-2 in two pairs of amphid neurons, left panel, and a portion show expression in other neurons besides of those, right panel. n=64.

FIG. 10*c* shows collocation of sul-2 neurons with FiTC stains. Upper panel shows colocalization in the head with the most anterior pair amphids, possibly ASK, ADF or ADL neurons, but not with the most posterior pair, ASG or ASE. In the tail, bottom panel, the four neurons where sul-2 is expressed colocalize with FiTC staining in PHAs and PHBs phasmids neurons.

FIG. 10*d* shows that identification of the two main pair of amphid where sul-2 is expressed by colocalization with the tph-1 neuron-specific promoter for ADF, upper panel, and the posterior neurons expressed by flp-6 promotor, ASE amphids, bottom panel. Scale bar 20 μm. In intestine, signals are unspecific from autofluorescence at the conditions imaged (cyan arrow heads).

FIG. 11*a* shows that an Integrated mCHERRY reporter of the sul-2 transcriptional unit is only expressed in sensory neurons, there is not expression in other tissues. Image in fluorescence and merged with the bright field image.

FIG. 11*b* shows inset of integrated worms, i) In heads, sul-2 is expressed in few amphid neurons (white arrows). In intestine, signals are unspecific from autofluorescence at the conditions imaged (cyan arrowheads). ii) There is not specific signals in vulva, embryos or proliferative germline zone. iii) There is not specific signals in gonad or mature oocytes. iv) In the tail, there is not significant signals in phasmids. Scale bar 50 μm.

FIG. 11*c* illustrates that apart from been expressed in the $Cl^-$ and Na+ sensing neuron (ASE), sul-2 mutants respond to $Cl^-$ similarly to wild type. Data from three independent replicates.

FIG. 11*d* illustrates that sul-2 mutants respond to Na+ similarly to wild type. tax-4 (p678) is a negative control. Data from three independent replicates. In all graphs Mean±SEM are displayed.

FIG. 11*e* illustrates that sul-2 deletion enhances longevity of the long-lived daf-10 (m79) mutant, which is affected in sensory neurons.

FIG. 12*a* illustrates that sul-2 has a beneficial effect during adulthood in muscular Parkinson's disease model. Data display from two independent biological replicates, n≥31 per day and condition.

FIG. 12*b* illustrates that sul-2 has less body bends to wild type control at same experimental conditions, n≥15 per day and condition (20° C.).

FIG. 12*c* illustrates that the protective effect of STX64 in muscular Parkinson's disease model is present throughout aging. Data display from two independent biological replicates, n≥12 per day and condition.

FIGS. 12*d* and 12*e* illustrate that sul-2 reduces significantly the number of α-synuclein aggregates in muscle at 7-day old. Photographs example of animals and quantifications, respectively. n=18. Scale bar 25 μm.

FIG. 12*f* illustrates that expression of human β-amyloid in muscle provokes paralysis with age (CL2006 strain) that is ameliorated in sul-2 deletion mutant.

FIG. 12*g* illustrates that expression of human β-amyloid in muscle provokes paralysis with age (CL2006 strain) that is ameliorated by STX64 treatment. Log-rank (Mantel-Cox) test, for sul-2 deletion p=0.0027 and STX treatment p=0.007.

FIG. 13*a* shows that paralysis phenotype of GMC101 strain, Alzheimer's disease model, is reduced with TS and ES, but do not with DHEAS (1 μg/ml). Assays performed with normal NGM plates. Data display from three independent biological replicates, n>130.

FIG. 13*b* shows that similar to daf-2(e1370); sul-2, percentage of L1 arrest in daf-2(e1370) increase with DHEAS, TS or ES.

FIGS. 13*c* and 13*d* illustrate that additional biological replicates of longevity curve with sulfated C19 steroid hormones. ES (1 μg/ml) increases lifespan in wild type background but does not increase further in sul-2(pv17), while DHEAS and TS do not affect (1 μg/ml).

DESCRIPTION OF THE INVENTION

Definitions

Figure 1:
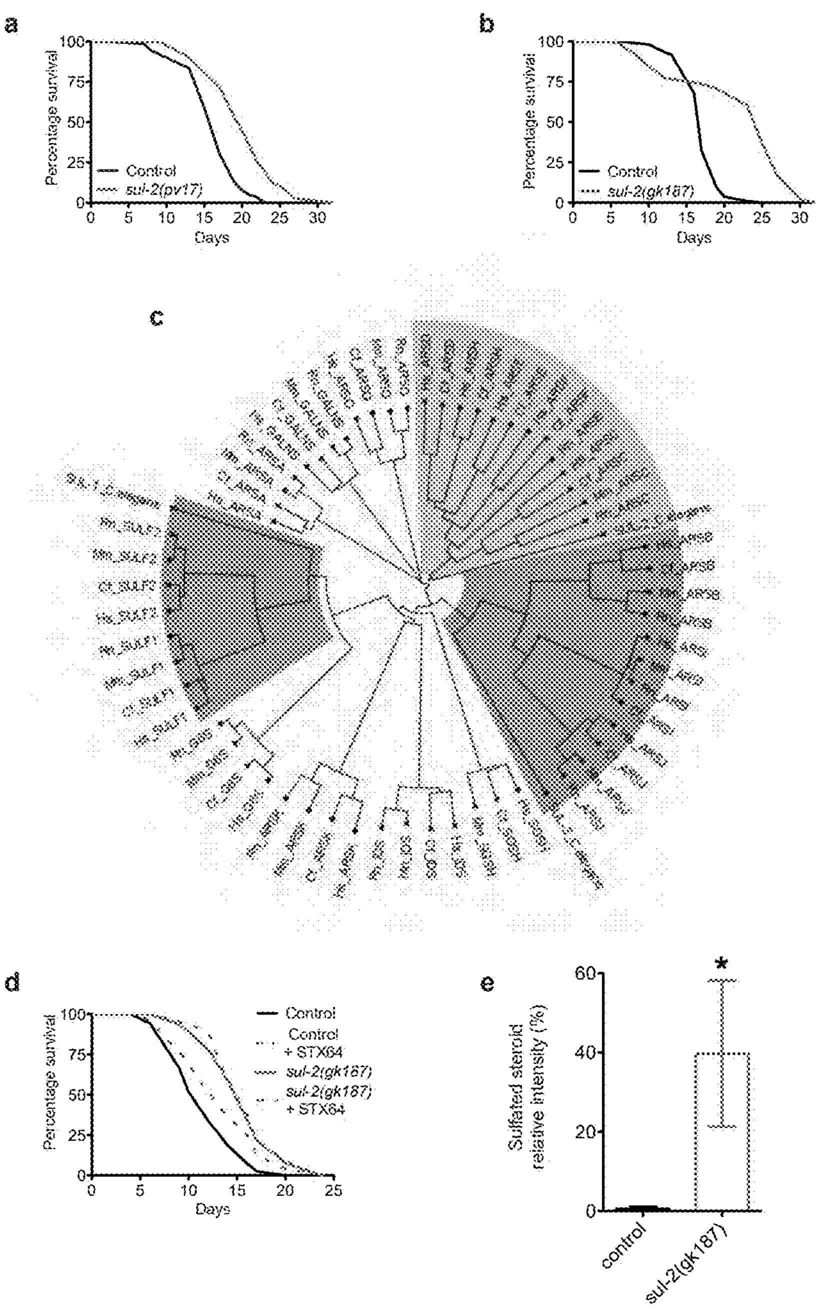
FIGS. 1*a*-1*e* illustrate that reduction of activity of sul-2 increases longevity and affects the levels of sulphated steroid hormones.

The terms "individual", "patient" or "subject" are used interchangeably in the present application to designate a human being and are not meant to be limiting in any way. The "individual", "patient" or "subject" can be of any age, sex and physical condition. The term "animal", as used in the present application, refers to any multicellular eukaryotic heterotroph which is not a human. In a preferred embodiment, the animal is selected from a group consisting of cats, dogs, pigs, ferrets, rabbits, gerbils, hamsters, guinea pigs, horses, worms, rats, mice, cows, sheep, goats, alpacas, camels, donkeys, llamas, yaks, giraffes, elephants, meerkats, lemurs, lions, tigers, kangaroos, koalas, bats, monkeys, chimpanzees, gorillas, bears, dugongs, manatees, seals and rhinoceroses.

As used herein, "pharmaceutically acceptable carrier" or "pharmaceutically acceptable diluent" means any and all solvents, dispersion media, coatings, antibacterial and antifungal agents, isotonic and absorption delaying agents, compatible with pharmaceutical administration. The term "pharmaceutically acceptable excipient" refers to any substance formulated alongside the active ingredient of a medication, included for the purpose of long-term stabilization, bulking up solid formulations that contain potent active ingredients in small amounts, or to confer a therapeutic enhancement on the active ingredient in the final dosage form, such as facilitating drug absorption, reducing viscosity, or enhancing solubility. Excipients can also be useful in the manufacturing process, to aid in the handling of the active substance concerned such as by facilitating powder flowability or non-stick properties, in addition to aiding in vitro stability such as prevention of denaturation or aggregation over the expected shelf life. The use of such media and agents for pharmaceutically active substances is well known in the art. Acceptable carriers, excipients, or stabilizers are nontoxic to recipients at the dosages and concentrations employed and, without limiting the scope of the present invention, include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone. Other pharmaceutically acceptable carriers, excipients, or stabilizers, such as those described in Remington: The Science and Practice of Pharmacy 22nd edition, Pharmaceutical press (2012), ISBN-13: 9780857110626 may also be included.

The terms "treatment" and "therapy", as used in the present application, refer to a set of hygienic, pharmacological, surgical and/or physical means used with the intent to cure and/or alleviate a disease and/or symptom with the goal of remediating the health problem. The terms "treatment" and "therapy" include preventive and curative methods, since both are directed to the maintenance and/or reestablishment of the health of an individual or animal. Regardless of the origin of the symptoms, disease and disability, the administration of a suitable medicament to alleviate and/or cure a health problem should be interpreted as a form of treatment or therapy within the context of this application.

The term "prevention", as used in the present application, refers to a set of hygienic, pharmacological, surgical and/or physical means used to prevent the onset and/or development of a disease and/or symptoms. The term "prevention" encompasses prophylactic methods, since these are used to maintain the health of an animal or individual.

The term "sulfatase inhibitor" refers to any substance capable of reducing the activity of an enzyme of the esterase class that catalyzes the hydrolysis of sulfate esters. The substance may be a molecule that binds to any of the following elements: the gene that encodes the sulfatase enzyme, transcription factors of said gene, any of the expression products of said gene, for example, without being limited thereto, the messenger RNA or the sulfatase enzyme, and decreases or inhibits the expression and the activity of the molecule to which it binds, and/or its intracellular or extracellular signaling, thereby leading to total or partial inhibition of the activity of the sulfatase enzyme. The inhibitor may be selected from the list consisting of, without being limited thereto: antagonists against the sulfatase enzyme (preferably chemical), silencing RNA or specific antibody against the sulfatase enzyme (preferably, the antibody is monoclonal); in the present invention, this antibody may be defined as a neutralizing antibody against the effect of the sulfatase enzyme. Examples of chemical inhibitors of the activity of the sulfatase enzyme are, without being limited thereto, alternative substrates such as those in the series 2-(hydroxyphenyl) indol sulfate, synthetic or natural steroids which present inhibitory activity against STS, such as 5-androstene-3β, 17β-diol-3 sulfate, competitive inhibitors such as E1-MTP or EMATE, non-oestrogenic inhibitors such as DU-14 (CAS NO: 186303-55-9), COUMATE (4-methylcoumarin-7-O-sulphamate) or STX64 (i.e., compound of Formula (II) as described in WO/2019243453), or others, such as KW-2581 or STX213, whose IC50 against the sulfatase enzyme has been determined in different studies (Purohit & Foster, 2012, J. Endocrinol., 212(2):99-110).

The term "steroid hormone sulfatase" ("STS") refers to any sulfatase enzyme involved in the metabolism of steroids. In particular, the enzymes catalyze the conversion of sulfated steroid precursors to the free steroid. An exemplary STS found in humans has been sequenced, characterized and the data have been deposited in the UniProtKB database under the accession number P08842. The term "steroid hormone sulfatase inhibitor" refers to any substance capable of reducing the activity of a steroid hormone sulfatase. The substance may be a molecule that binds to any of the following elements: the gene that encodes the STS enzyme, transcription factors of said gene, any of the expression products of said gene, for example, without being limited thereto, the messenger RNA or the STS enzyme, and decreases or inhibits the expression and the activity of the molecule to which it binds, and/or its intracellular signaling, thereby leading to total or partial inhibition of the activity of the STS enzyme. The inhibitor may be selected from the list consisting of, without being limited thereto: antagonists against the STS enzyme (preferably chemical), silencing RNA or specific antibody against the STS enzyme (preferably, the antibody is monoclonal); in the present invention, this antibody may be defined as a neutralising antibody against the effect of the STS enzyme. Examples of chemical inhibitors of the activity of the STS enzyme are, without being limited thereto, alternative substrates such as those in the series 2-(hydroxyphenyl) indol sulfate, synthetic or natural steroids which present inhibitory activity against STS, such as 5-androstene-3β, 17β-diol-3 sulfate, competitive inhibitors such as E1-MTP or EMATE, non-oestrogenic inhibitors such as DU-14, COUMATE (4-methylcoumarin-7-O-sulphamate) or STX64 (i.e., compound of Formula (II) as described in WO/2019243453), or others, such as KW-2581 or STX213, whose IC50 against the sulfatase enzyme has been determined in different studies (Purohit & Foster, 2012, J. Endocrinol., 212(2):99-110).

The terms "protein-aggregation disease", "proteopathy", "proteinopathy" or "protein misfolding diseases" refers to any disease in which certain proteins become structurally abnormal and thereby disrupt the function of cells, tissues and organs of the body. Often the proteins fail to fold into their normal configuration; in this misfolded state, the proteins can become toxic in some way or they can lose their normal function. Non-limiting examples of protein-aggregation diseases include systemic AL amyloidosis, Alzheimer's Disease, Diabetes mellitus type 2, Parkinson's disease, Transmissible spongiform encephalopathy e.g. Bovine spongiform encephalopathy, Fatal Familial Insomnia, Huntington's Disease, Medullary carcinoma of the thyroid, Cardiac arrhythmias, Atherosclerosis, Rheumatoid arthritis, Aortic medial amyloid, Prolactinomas, Familial amyloid polyneuropathy, Hereditary non-neuropathic systemic amyloidosis, Dialysis related amyloidosis, Finnish amyloidosis, Lattice corneal dystrophy, Cerebral amyloid angiopathy, Cerebral amyloid angiopathy (Icelandic type), Sporadic Inclusion Body Myositis, Amyotrophic lateral sclerosis (ALS), Prion-related or Spongiform encephalopathies, such as Creutzfeld-Jacob, Dementia with Lewy bodies, Frontotemporal dementia with Parkinsonism, Spinocerebellar ataxias, Spinocerebellar ataxia, Spinal and bulbar muscular atrophy, Hereditary dentatorubral-pallidoluysian atrophy, Familial British dementia, Familial Danish dementia, Non-neuropathic localized diseases, such as in Type II diabetes mellitus, Medullary carcinoma of the thyroid, Atrial amyloidosis, Hereditary cerebral hemorrhage with amyloidosis, Pituitary prolactinoma, Injection-localized amyloidosis, Aortic medial amyloidosis, Hereditary lattice corneal dystrophy, Corneal amyloidosis associated with trichiasis, Cataract, Calcifying epithelial odontogenic tumors, Pulmonary alveolar proteinosis, Inclusion-body myositis, Cutaneous lichen amyloidosis, and Non-neuropathic systemic amyloidosis, such as AL amyloidosis, AA amyloidosis, Familial Mediterranean fever, Senile systemic amyloidosis, Familial amyloidotic polyneuropathy, Hemodialysis-related amyloidosis, ApoAI amyloidosis, ApoAII amyloidosis, ApoAIV amyloidosis, Finnish hereditary amyloidosis, Lysozyme amyloidosis, Fibrinogen amyloidosis, Icelandic hereditary cerebral amyloid angiopathy, familial amyloidosis, and systemic amyloidosis which occurs in multiple tissues, such as light-chain amyloidosis, and other various neurodegenerative disorders.

The term "protein aggregate" refers to any accumulation of abnormally folded proteins which cause and/or are associated with the negative progression of a protein-aggregation disease.

The term "amyloid" refers to a form of protein aggregates wherein the aggregates form unbranched fibers that bind Congo Red and then show green birefringence when viewed between crossed polarizers (for example, see Eisenberg & Jucker, 2012. Cell. 148(6):1188-203 and Sipe et al., 2012. Amyloid. 19(4):167-70).

The term "oligomer" refers to any accumulation of abnormally folded proteins which cause and/or are associated with the negative progression of a protein-aggregation disease and does not satisfy the definition of an amyloid. For example, polyglutamine oligomers cause and/or are associated with the negative progression of Huntington's disease (see Hoffner & Dijan, 2014. Brain Sci. 4 (1): 91-122).

DESCRIPTION

Gonad is a key tissue in the regulation of life span. Germline regulates longevity by inhibiting the production of dafachronic acid in the somatic gonads. Consistently, germline ablation or mutations that abolish the generation of germline, increase life span by activation of dafachronic acid synthesis. Gonads are also the classical tissue that produces sex steroids, although is not the only one. Our data indicates that inhibition of the sulfatase activity either by mutation or by STX64 raises the level of a very specific set of sulfated steroid hormones, which in fact generate an increase in longevity. This increase in longevity depends on common factors involved in life span extension produced by germline loss, suggesting that both processes are in fact linked. We cannot distinguish whether the pro-longevity effect of sulfated steroid hormones participates in the same pathway or acts in parallel to the germline longevity sharing some element of this pathway. The fact that sul-2 inhibition does not depend on NHR-49, or only partially depends on NHR-80, which are essentials for germline-mediated longevity, point to the second option.

We have also studied the level of sulfated steroid hormones in the germline less glp-1 mutant, and we do not observe an increase in sulfated hormones. Those data favor the idea that gonads produce steroid hormones, which are modified by sulfation. These sulfated steroid hormones, probably altering neurotransmission, produce an increase in longevity, through common factors to germline-less animals. The fact that the enzymes involved in the sulfate modification of steroid hormones (sulfatase SUL-2 and sulfotranferase SSU-1) are expressed in sensory neurons suggests that alteration the sulfate state of hormones may act in the integration of environmental cues, such as nutrient availability, with the reproductive status, which are two-linked processes.

In *C. elegans*, cell proliferation of the somatic cells only occurs during development and in larval stages but not in the adult stage; Therefore, increasing longevity is due to the maintenance of the postmitotic cells. One of the stresses observed in *C. elegans* adult cells is the aggregation of endogenous proteins, which generates cellular misfunction. This age-related formation of aggregates is also observed upon ectopic expression of aggregation-prone proteins, like β-amyloid or α-synuclein. Long-lived mutants such as daf-2 or glp-1 delay the aggregation toxicity through a different mechanism including chaperon expression and degradation by proteasome or autophagy. We herein show that inhibition of the sulfatase activity or treatment with some specific sulphated C19 androgen hormones impinge not only in longevity but also reduce protein aggregation and its toxic consequences in *C. elegans* models of protein aggregation diseases.

Regulation of steroid hormones by sulfation is a conserved process. In mammals, sulfotransferases and sulfatases are expressed in different tissues, including the nervous system, similar to what we observe in *C. elegans*. In humans, C19 steroid hormones have also been involved in longevity. For instance, dehydroepiandrosterone sulfate (DHEAS) declines with age and has been used as a marker of aging, raising speculations of a causative effect on sarcopenia, poor cognitive function and other aging associated diseases6 including Alzheimer's disease. Our data show that inhibition of the steroid sulfatase by mutation or by STX64 treatment extends lifespan in *C. elegans* and protects against aging-associated proteotoxicity in nematodes. Interestingly, similar effects were observed upon treatment with some specific sulfated C19 steroid hormones.

Figure 4:
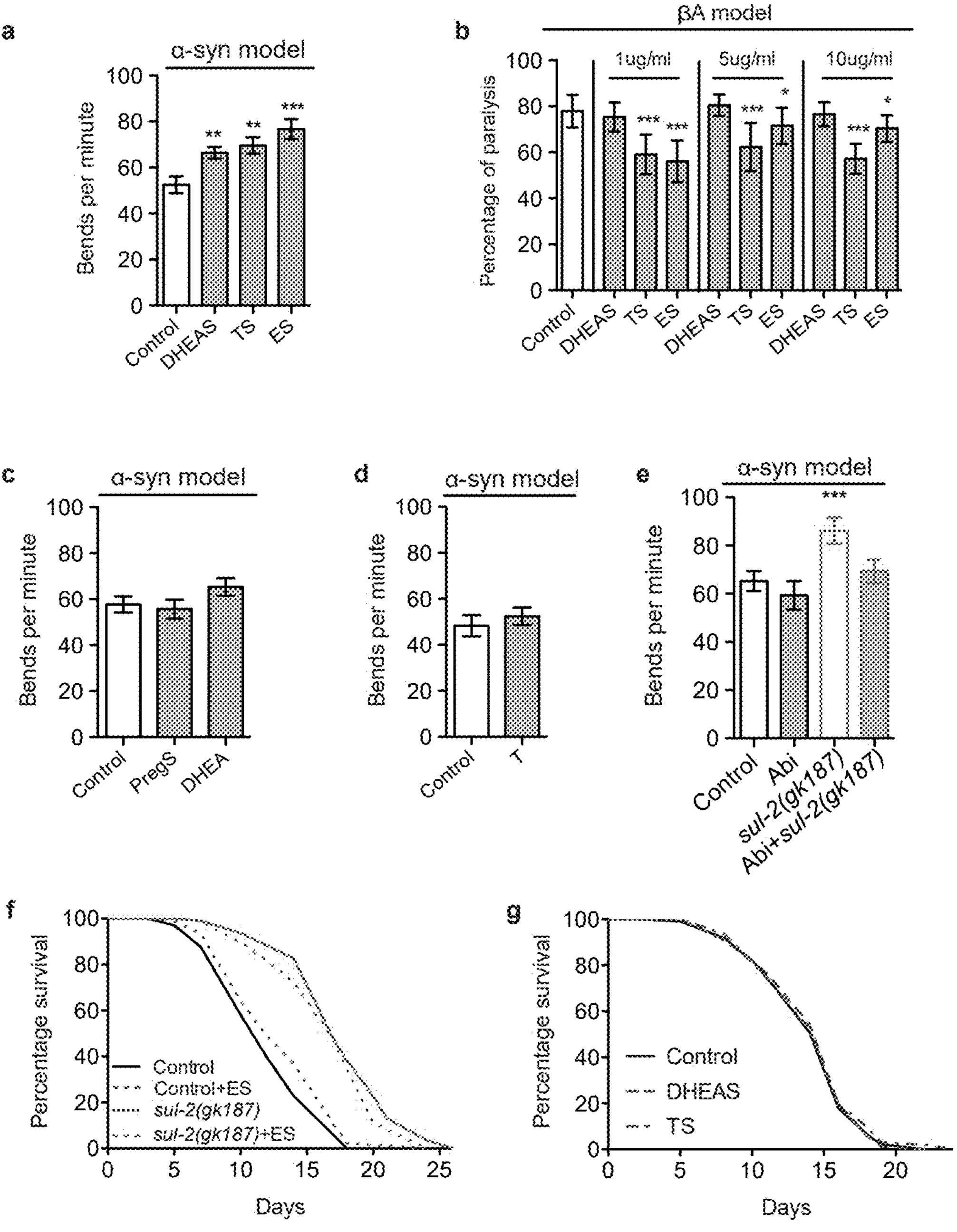
FIGS. 4*a*-4*g* illustrate sulfated C19 androgen steroid hormones mimic sul-2 inactivation.
Figure 13:
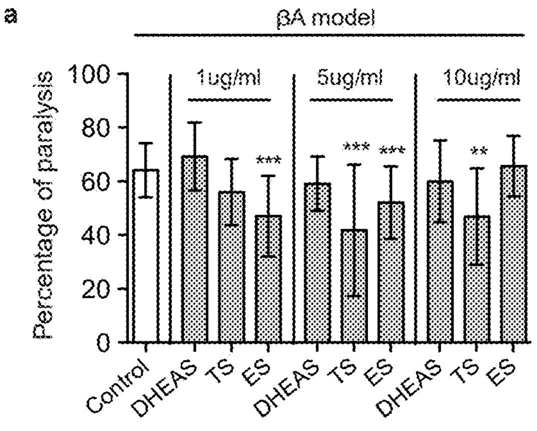
FIGS. 13*a*-13*d* show treatment with sulfated C19 steroid hormones phenocopy sul-2 inactivation.
Figure 13:
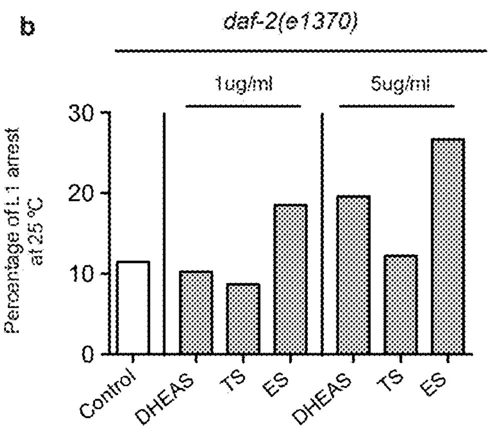
Figure 13:
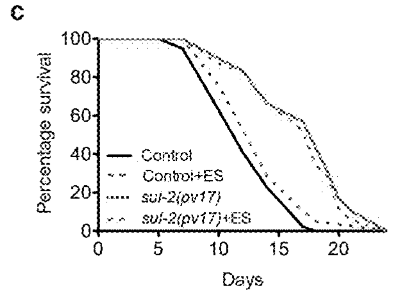
Figure 13:
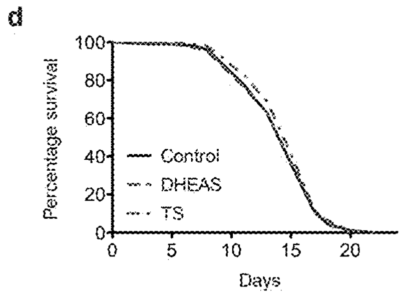
Figure 14:
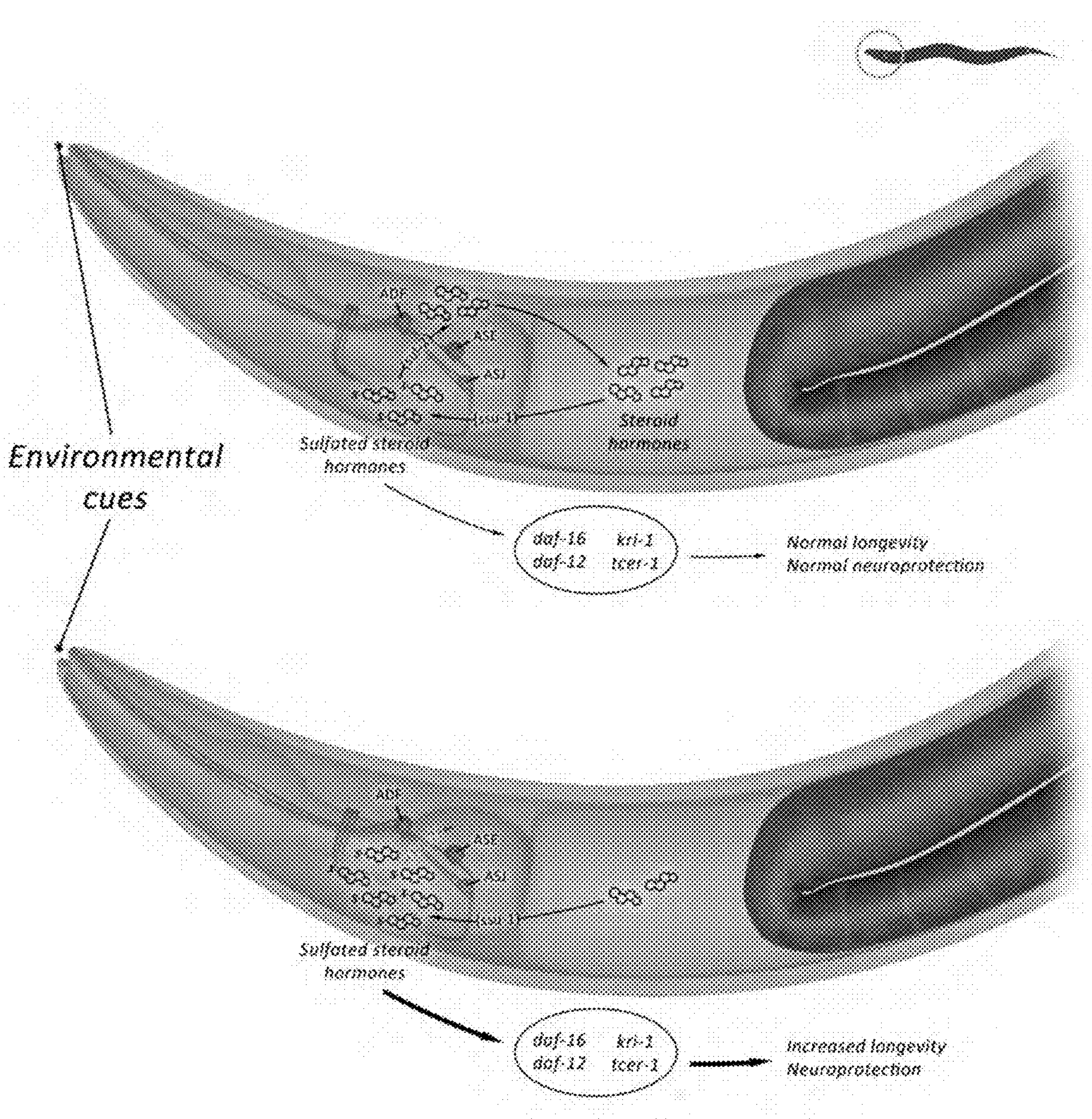
FIG. 14 shows model of regulation of longevity by SUL-2. The sulfatase SUL-2 and the sulfotransferase (probably ssu-1) regulates the level of sulfated steroid hormones. High level of sulfated steroid hormone provokes an increase of longevity, which depend on the same factors to the longevity generated by germline reduction (daf-16, daf-12, kri-1, tcer-1). The fact that both sulfatase and sulfotransferase are expressed in sensory neurons suggests a coordination of the sulfated state of the hormones with environmental signals.
Figure 15:
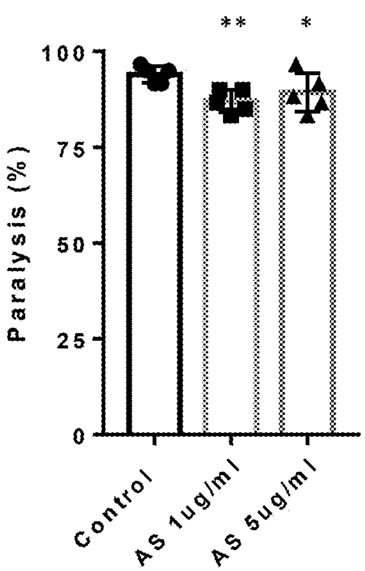
FIG. 15 illustrates that treatment with Androsterone Sulfate (AS) ameliorates the symptoms of Alzheimer's model in *Caenorhabditis elegans*. The strain GMC101 expresses the human b-amyloid in muscle cells and generate paralysis with age. Treatment with 1 μg/ml or 5 μg/ml reduce this effect. Data from 5 biological replicates. Paralysis was monitored during adulthood. Paralysis was considered when nematodes did not move after stimulation with a platinum pick. More than 200 nematodes were analyzed. Nematodes were synchronized and assayed at 20° C.

More particularly and in connection to said specific sulfated C19 steroid hormones, in mammals, sulfated hormones have been long considered inactive forms that function mainly as reservoirs and are activated by steroid sulfatases, In the present invention, in order to sort out whether the beneficial effect of sul-2 inhibition is due to the reduction of non-sulfated hormones or the increase of sulfated hormones, we tested the commercially available sulfated steroid hormones that are highly presented in the mutant (Table 1). We observed that the C19 androgens dehydroepiandrosterone sulfate (DHEAS), testosterone sulfate (TS) and epitestosterone sulfate (ES) improved the mobility in the Parkinson model of *C. elegans*, with a remarkable result for ES (FIG. 4*a*). Similar results were obtained in the Alzheimer model with TS and ES but not with DHEAS (FIG. 4*b* and FIG. 13*a*). Non-sulfated DHEA or non-sulfated testosterone showed no effect, neither pregnenolone sulfate, which belongs to the C21 group of steroid hormones (FIG. 4*c-d*). These results indicate that at least some sulfated C19 androgens are involved in the protective effect against protein aggregation diseases and strongly suggest that the beneficial effect of sul-2 inhibition is due to the increased levels of this type of hormones. In agreement with these results, treatment with the antiandrogenic compound abiraterone (Abi) 36, did not affect wild type animals but suppressed the beneficial effect of sul-2 mutation (FIG. 4*e*).

We then tested if those hormones are also involved in the other phenotypes observed in the sul-2 mutant. Treatment with any of those sulfated hormones generated an increase of L1 arrest in a daf-2(e1370) background as observed in sul-2 or STX 64 treated animals (FIG. 13*b*). Interestingly, treatment with ES, but not TS or DHEAS, increased in longevity on a wild type background and did not further increase longevity in sul-2 mutants backgrounds (FIG. 4*f-g* and FIG. 13*c-d*), indicating that both interventions share the same molecular mechanism. Thus, addition of ES recapitulated all the phenotypes described for sul-2 inhibition and strongly suggesting that the causative effect of sul-2 mutation is due to the increase of C19 androgen sulphated hormones related to ES.

Therefore, a first aspect, the present invention provides a composition, including a pharmaceutical or nutraceutical composition or a Dietary Supplement, comprising a sulfated C19 androgen for use in the treatment and/or prevention of a protein-aggregation disease.

In a second aspect, the present invention provides a kit for use in the manufacture of a medicament for the treatment and/or prevention of a protein-aggregation disease comprising a (i) a sulfated C19 androgen; and (ii) pharmaceutically acceptable carrier and/or diluent. In a preferred embodiment, the kit further comprises a pharmaceutically acceptable excipient.

Preferred embodiments for the kits and compositions of the present invention are provided below.

Sulfated C19 Androgens of the Present Invention

In a preferred embodiment, the sulfated C19 androgen is dehydroepiandrosterone sulfate (DHEAS), testosterone sulfate (TS), epitestosterone sulfate (ES) or Androsterone sulfate (AS). In a more preferred embodiment, the sulfatase inhibitor is selected from the group consisting of testosterone sulfate (TS), epitestosterone sulfate (ES) or Androsterone sulfate (AS).

Testosterone sulfate (TS) (pubchem.ncbi.nlm.nih.gov) is an endogenous, naturally occurring steroid and minor urinary metabolite of testosterone, of chemical name [(8R,9S,10R,13S,14S,17S)-10,13-dimethyl-3-oxo-1,2,6,7,8,9,11,12,14,15,16,17-dodecahydrocyclopenta[a]phenanthren-17-yl] hydrogen sulfate, and formula:

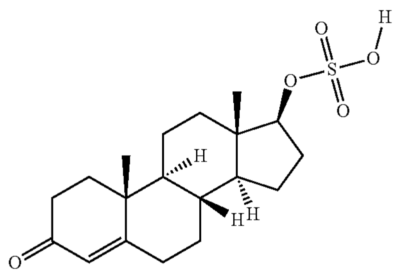

Other names. Testosterone 17β-sulfate; Testosterone 17β-sulfuric acid; 17β-(Sulfooxy)androst-4-en-3-one.

Epitestosterone structurally differs from testosterone only in the configuration at the hydroxy-bearing carbon, C17. Epitestosterone sulfate (ES) also known as Testosterone 17α-sulfate has the following chemical name N,N-diethylethanamine; [(8R,9S,10R,13S,14S,17R)-10,13-dimethyl-3-oxo-1,2,6,7,8,9,11,12,14,15,16,17-dodecahydrocyclopenta[a]phenanthren-17-yl] hydrogen sulfate, and formula:

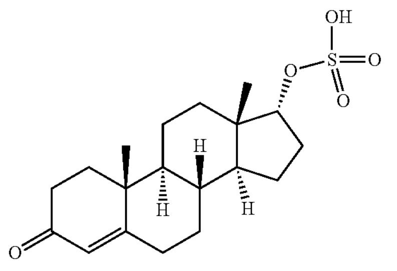

Androsterone sulfate (AS) also known as 3α-hydroxy-5α-androstan-17-one 3α-sulfate, is an endogenous, naturally occurring steroid and one of the major urinary metabolites of androgens. It is a steroid sulfate which is formed from sulfation of androsterone by the steroid sulfotransferase SULT2A1 and can be de-sulfated back into androsterone by steroid sulfatase, of chemical name [(3R,5S,8R,9S,10S,13S,14S)-10,13-Dimethyl-17-oxo-1,2,3,4,5,6,7,8,9,11,12,14,15,16-tetradecahydrocyclopenta[a]phenanthren-3-yl] sulfate, and formula hydrogen

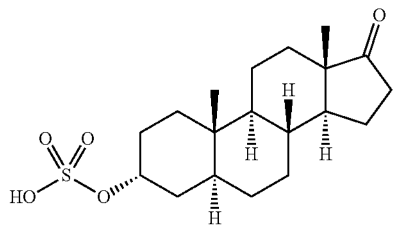

It is herein noted that any of the above mentioned sulfated C19 androgens includes the corresponding salts and esters thereof. Preferably any of the above mentioned sulfated C19 androgens includes the corresponding pharmaceutically acceptable salts, pharmaceutically acceptable solvates, isotopic variants (preferably comprising deuterium atoms and/or one or more carbon atoms with 13C), different crystalline forms such as polymorphs, pharmaceutically acceptable esters, stereoisomers, tautomers, analogs and derivatives thereof.

Solvates such as (A) or (B), where R=H, alkyl or aryl and are formed by addition of water or an alcohol to the parent compound:

(A)

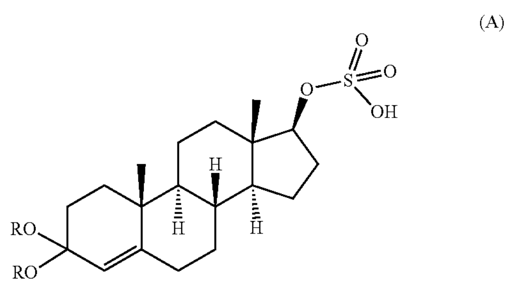

(B)

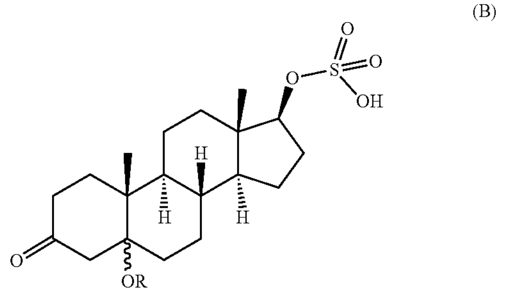

Isotopic variants for example where one or more atoms are replaced with a stable isotope of the same atom, such as replacing one or more hydrogen atoms by deuterium atoms, for example (C), or one or more carbon atoms with 13C for example (D). It will be appreciated this possibility can apply to any atom within the structures, and also combinations can be considered:

(C)

(D)

(E)

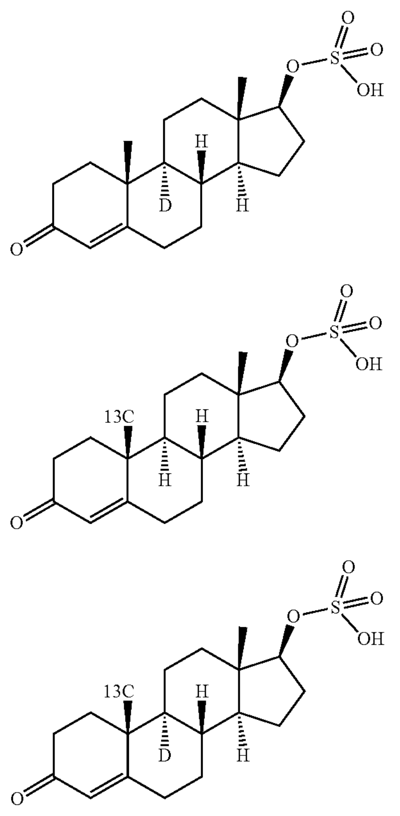

Protein-Aggregation Disease

Protein aggregates such as amyloids and oligomers have been associated with a number of diseases. In some cases, these protein aggregates can become toxic and can cause significant damage to cells and tissue. This toxicity is thought to be one of the contributing factors causing and/or contributing to the pathology of protein-aggregation diseases.

Further, the abnormal processing and folding of a protein linked to a protein-aggregation disease can start decades before the outward symptoms of the protein-aggregation disease can be observed (Jack et al., 2010. Lancet Neurol. 9(1):119-28). Thus, in a preferred embodiment, amyloids and/or oligomers are removed, and/or their formation is prevented in the patient and/or animal as a result of administering any one of the compositions of the present invention, preferably any composition, including pharmaceutical or nutraceutical compositions or Dietary Supplements. Further, in a preferred embodiment, the sulfated C19 androgens treats and/or prevents proteotoxicity in a protein-aggregation disease. The term "proteotoxicity" refers to any impairment of cell function caused by misfolding of a protein.

By directly targeting the formation of protein aggregates, the compositions and kits of the present invention are able to treat and/or prevent a protein-aggregation disease in patients and/or animals who are at the early stages of a protein-aggregation disease but still do not show any outward symptoms. Further, the compositions and kits of the present invention also treat the advanced stages of a protein-aggregation disease.

In a preferred embodiment, the patient and/or animal have undergone the pathophysiological changes that cause protein aggregation but have not yet reached the stage of the disease where outward symptoms are observable. In other words, the patient and/or animal is at an early stage of the disease. The term "outward symptom" refers to any symptom which can be observed by a physician using any non-invasive procedure.

In a preferred embodiment, the sulfated C19 androgens slows down the progression of a protein-aggregation disease by inhibiting the formation of protein aggregates and/or the sulfated C19 androgens delays the onset of a protein-aggregation disease by inhibiting the formation of protein aggregates.

In a preferred embodiment, the protein-aggregation disease is selected from a list consisting of systemic AL amyloidosis, Alzheimer's Disease, Diabetes mellitus type 2, Parkinson's disease, Transmissible spongiform encephalopathy e.g. Bovine spongiform encephalopathy, Fatal Familial Insomnia, Huntington's Disease, Medullary carcinoma of the thyroid, Cardiac arrhythmias, Atherosclerosis, Rheumatoid arthritis, Aortic medial amyloid, Prolactinomas, Familial amyloid polyneuropathy, Hereditary non-neuropathic systemic amyloidosis, Dialysis related amyloidosis, Finnish amyloidosis, Lattice corneal dystrophy, Cerebral amyloid angiopathy, Cerebral amyloid angiopathy (Icelandic type), Sporadic Inclusion Body Myositis, Amyotrophic lateral sclerosis (ALS), Prion-related or Spongiform encephalopathies, such as Creutzfeld-Jacob, Dementia with Lewy bodies, Frontotemporal dementia with Parkinsonism, Spinocerebellar ataxias, Spinocerebellar ataxia, Spinal and bulbar muscular atrophy, Hereditary dentatorubral-pallidoluysian atrophy, Familial British dementia, Familial Danish dementia, Non-neuropathic localized diseases, such as in Type II diabetes mellitus, Medullary carcinoma of the thyroid, Atrial amyloidosis, Hereditary cerebral hemorrhage with amyloidosis, Pituitary prolactinoma, Injection-localized amyloidosis, Aortic medial amyloidosis, Hereditary lattice corneal dystrophy, Corneal amyloidosis associated with trichiasis, Cataract, Calcifying epithelial odontogenic tumors, Pulmonary alveolar proteinosis, Inclusion-body myositis, Cutaneous lichen amyloidosis, and Non-neuropathic systemic amyloidosis, such as AL amyloidosis, AA amyloidosis, Familial Mediterranean fever, Senile systemic amyloidosis, Familial amyloidotic polyneuropathy, Hemodialysis-related amyloidosis, ApoAI amyloidosis, ApoAII amyloidosis, ApoAIV amyloidosis, Finnish hereditary amyloidosis, Lysozyme amyloidosis, Fibrinogen amyloidosis, Icelandic hereditary cerebral amyloid angiopathy, familial amyloidosis, and systemic amyloidosis which occurs in multiple tissues, such as light-chain amyloidosis, and other various neurodegenerative disorders. Preferably, the protein-aggregation disease is selected from a list consisting of Alzheimer's disease, Parkinson's disease and Huntington's disease. In a preferred embodiment, the protein-aggregation disease is not Alzheimer's disease and/or a type of cancer.

In a preferred embodiment, the protein-aggregation disease is selected from a list consisting of Alzheimer's disease, Parkinson's disease and Huntington's disease and the sulfated C19 androgens of the present invention are preferably selected from the list consisting of testosterone sulfate (TS), epitestosterone sulfate (ES) or Androsterone sulfate (AS). More preferably, said sulfated C19 androgens are in the form of a pharmaceutical or nutraceutical composition or in the form of Dietary Supplements.

In a preferred embodiment, the protein-aggregation disease is a central nervous system localized protein-aggregation disease. In a preferred embodiment, the protein-aggregation disease is also a neurodegenerative disease. The term "neurodegenerative disease" refers to any disorder characterized by the progressive loss of structure or function of neurons, including death of neurons. For example, Alzheimer's disease is an example or a protein-aggregation disease and an example of a neurodegenerative disease.

Combined Embodiments of Sulfatase Inhibitors and Protein-Aggregation Diseases

In a preferred embodiment, the present invention refers to a combination of the sulfated C19 androgens of the present invention, preferably testosterone sulfate (TS), epitestosterone sulfate (ES) or Androsterone sulfate (AS), and a sulfatase inhibitor selected from the list consisting of 2-(hydroxyphenyl) indol sulfate, 5-androstene-3β, DU-14, 17β-diol-3 sulfate, E1-MTP, EMATE, COUMATE, STX64, KW-2581, STX213, morpholine, silencing RNA and specific antibody against the STS enzyme; or the sulfatase inhibitor of Formula (I):

(I)

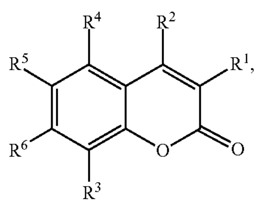

wherein:

(a) $R_1$-$R_6$ are independently selected from hydrogen, halogen (fluorine, chlorine, bromine, iodine or astatine), hydroxyl, sulfamate ($OSO_2NH_2$), alkyl and salts thereof;

(b) at least one of $R_1$-$R_6$ is a sulfamate group; and two or more of $R_1$-$R_6$ are linked together to form an additional cyclic structure; and for use in the prevention or treatment of a protein-aggregation disease, preferably selected from a list consisting of Alzheimer's disease, Huntington's disease and Parkinson's disease.

In a preferred embodiment, the sulfatase inhibitor is STX64 (i.e., the compound of Formula (II) as described in WO/2019243453) and the combination is for use in the prevention or treatment of a protein-aggregation disease selected from a list consisting of Alzheimer's disease, Huntington's disease and Parkinson's disease. In a preferred embodiment, the sulfatase inhibitor is STX64 and the protein-aggregation disease is Alzheimer's disease. In a preferred embodiment, the sulfatase inhibitor is STX64 and the protein-aggregation disease is Huntington's disease. In a preferred embodiment, the sulfatase inhibitor is STX64 and the protein-aggregation disease is Parkinson's disease.

It is noted that the sulfatase inhibitor of Formula (II) as described in WO/2019243453 (STX64) is the compound of Formula:

(II)

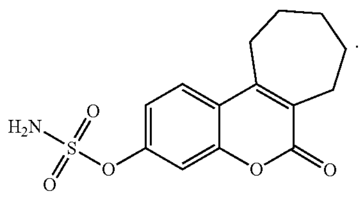

Including any salts thereof, preferably any pharmaceutically acceptable salts thereof.

Pharmaceutical Compositions

In a preferred embodiment, the composition is a pharmaceutical composition optionally further comprising a pharmaceutically acceptable carrier and/or diluent. Preferably, the pharmaceutical composition may further comprise a pharmaceutically acceptable excipient.

A pharmaceutical composition as described herein may also contain other substances. These substances include, but are not limited to, cryoprotectants, lyoprotectants, surfactants, bulking agents, anti-oxidants, and stabilizing agents. In some embodiments, the pharmaceutical composition may be lyophilized.

The term "cryoprotectant" as used herein, includes agents which provide stability to the compositions against freezing-induced stresses. Cryoprotectants may also offer protection during primary and secondary drying and long-term product storage. Non-limiting examples of cryoprotectants include sugars, such as sucrose, glucose, trehalose, mannitol, mannose, and lactose; polymers, such as dextran, hydroxyethyl starch and polyethylene glycol; surfactants, such as polysorbates (e.g., PS-20 or PS-80); and amino acids, such as glycine, arginine, leucine, and serine. A cryoprotectant exhibiting low toxicity in biological systems is generally used.

In one embodiment, a lyoprotectant is added to a pharmaceutical composition described herein. The term "lyoprotectant" as used herein, includes agents that provide stability to the compositions during the freeze-drying or dehydration process (primary and secondary freeze-drying cycles. This helps to minimize product degradation during the lyophilization cycle, and improve the long-term product stability. Non-limiting examples of lyoprotectants include sugars, such as sucrose or trehalose; an amino acid, such as monosodium glutamate, non-crystalline glycine or histidine; a methylamine, such as betaine; a lyotropic salt, such as magnesium sulfate; a polyol, such as trihydric or higher sugar alcohols, e.g., glycerin, erythritol, glycerol, arabitol, xylitol, sorbitol, and mannitol; propylene glycol; polyethylene glycol; pluronics; and combinations thereof. The amount of lyoprotectant added to a pharmaceutical composition is generally an amount that does not lead to an unacceptable amount of degradation when the pharmaceutical composition is lyophilized.

In some embodiments, a bulking agent is included in the pharmaceutical composition. The term "bulking agent" as used herein, includes agents that provide the structure of the freeze-dried product without interacting directly with the pharmaceutical product. In addition to providing a pharmaceutically elegant cake, bulking agents may also impart useful qualities in regard to modifying the collapse temperature, providing freeze-thaw protection, and enhancing the stability over long-term storage. Non-limiting examples of bulking agents include mannitol, glycine, lactose, and sucrose. Bulking agents may be crystalline (such as glycine, mannitol, or sodium chloride) or amorphous (such as dextran, hydroxyethyl starch) and are generally used in formulations in an amount from 0.5% to 10%.

Other pharmaceutically acceptable carriers, excipients, or stabilizers, such as those described in Remington's Pharmaceutical Sciences 16th edition, Osol, A. Ed. (1980) or *Remington: The Science and Practice of Pharmacy* 22$^{nd}$ edition, Pharmaceutical press (2012), ISBN-13: 9780857110626 may also be included in a pharmaceutical composition described herein, provided that they do not adversely affect the desired characteristics of the pharmaceutical composition.

For solid pharmaceutical compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For solution for injection, the pharmaceutical composition may further comprise cryoprotectants, lyoprotectants, surfactants, bulking agents, anti-oxidants, stabilizing agents and pharmaceutically acceptable carriers. For aerosol administration, the pharmaceutical compositions are generally supplied in finely divided form along with a surfactant and propellant. The surfactant must, of course, be nontoxic, and is generally soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. For suppositories, traditional binders and carriers may include, for example, polyalkalene glycols or triglycerides.

In a preferred embodiment, the composition the present invention is prepared for oral, sublingual, buccal, intranasal, intravenous, intramuscular, intraperitoneal and/or inhalation-mediated administration.

It is noted that compositions other from pharmaceutical compositions, including nutraceutical compositions or a Dietary Supplements, are also part of the invention Administration The compositions of the present invention, including pharmaceutical or nutraceutical compositions or Dietary Supplements, may be administered using any route known to the skilled person. In a preferred embodiment, the composition of the present invention is administered transdermally, sublingually, intravenously, intranasally, intracerebroventricularly, intraarterially, intracerebrally, intramuscularly, intraperitoneally, orally or via inhalation.

In a preferred embodiment, the composition of the present invention is administered transdermally, sublingually, intravenously, intraperitoneally, orally or via inhalation. Where the composition is administered via inhalation, the composition may be aerosolized and administered via, for example, an anesthesia mask.

In a preferred embodiment, the composition of the present invention is administered transdermally, sublingually, intravenously, subcutaneously, orally or via inhalation. Preferably, the composition is administered orally or sublingually.

In a preferred embodiment, the composition comprises a therapeutically effective amount of the sulfated C19 androgens of the present invention, preferably testosterone sulfate (TS), epitestosterone sulfate (ES) or Androsterone sulfate (AS). The term "therapeutically effective amount" refers to an amount of the sulfated C19 androgens of the present invention, preferably testosterone sulfate (TS), epitestosterone sulfate (ES) or Androsterone sulfate (AS), in a composition which has a therapeutic effect and which is able to treat and/or prevent a protein-aggregation disease.

In a preferred embodiment, the composition is used in a combination therapy with any other treatment or therapy commonly used to treat and/or prevent a protein-aggregation disease. In a preferred embodiment, the composition is used in a combination therapy with a sulfatase inhibitor selected from the list consisting of 2-(hydroxyphenyl) indol sulfate, 5-androstene-3β, DU-14, 17β-diol-3 sulfate, E1-MTP, EMATE, COUMATE, STX64, KW-2581, STX213, morpholine, silencing RNA and specific antibody against the STS enzyme; or the sulfatase inhibitor of Formula (I):

(I)

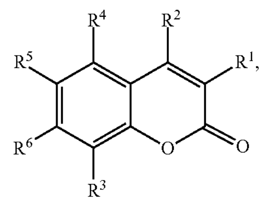

wherein:

(a) $R_1$-$R_6$ are independently selected from hydrogen, halogen (fluorine, chlorine, bromine, iodine or astatine), hydroxyl, sulfamate ($OSO_2NH_2$), alkyl and salts thereof;

(b) at least one of $R_1$-$R_6$ is a sulfamate group; and two or more of $R_1$-$R_6$ are linked together to form an additional cyclic structure.

In a preferred embodiment, the sulfatase inhibitor is STX64 (i.e., the compound of Formula (II) as described in WO/2019243453)

The compositions of the present invention may be administered once or more than once. A skilled person will be able to ascertain the most effective dosage regimen for the patient. For example, the most effective dosage regimen may be one where the patient is administered the composition twice daily, once a day, once every three days, once a week, once a month, once every three months, once every six months or once every year.

The following examples merely illustrate the present invention but do not limit the same.

Examples

Identification of sul-2 as a Regulator of Longevity

Unravelling new elements that govern the genetic control of aging is key to improve our understanding of this intricate biological process and improve human healthspan. To this aim, we isolated *Caenorhabditis elegans* thermotolerant mutants and identified an allele pv17 of the sul-2 gene, which encodes one of the three members of the *C. elegans* sulfatase family8.

Figure 5:
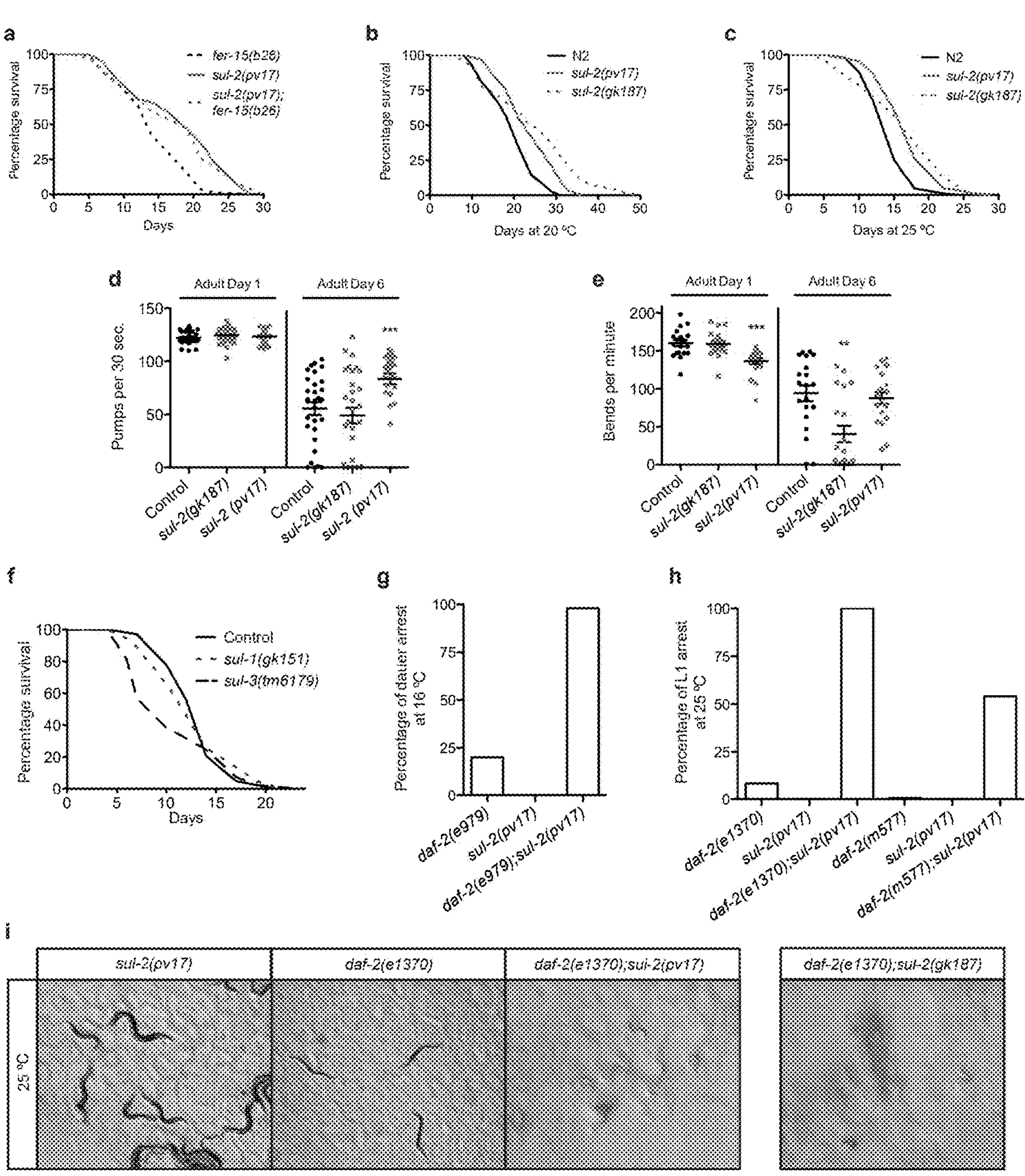
FIGS. 5*a*-5*i* illustrate that longevity assays of sul-2 and genetic interactions with daf-2. sul-2 mutants do not show visible phenotypes but are long-lived and enhance developmental phenotypes of daf-2 mutants.
Figure 6:
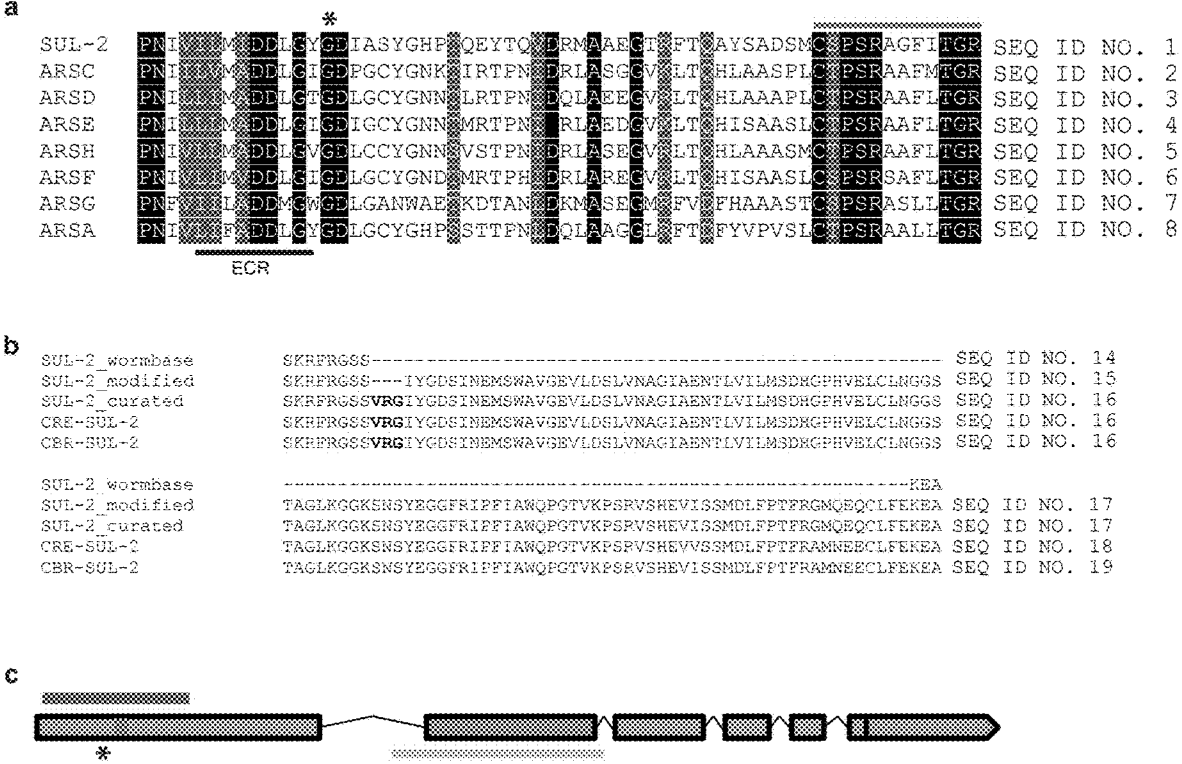
FIGS. 6*a*-6*c* show an identification of pv17 allele and curated sequence of SUL-2 (SEQ ID NO. 16).

Worms carrying either the isolated (pv17) allele or the null allele (gk187) of sul-2 lived longer than wild type although the gk187 allele showed a bimodal curve with a subpopulation that had an early mortality (FIG. 1*a-b*, and FIG. 5*a*). Pumping frequency and mobility during aging declined similar or slower than wild type, overall for the pv17 allele, suggesting a healthier life span (FIG. 5*d-e*). Deletion of the other two sulfatases genes, sul-1 and sul-3, did not increase lifespan, indicating that the sulfatase sul-2 has a main role in the regulation of longevity (FIG. 5*f*). Mutations in sul-2 also enhanced the developmental phenotypes of mutants in the insulin/insulin like growth factor (IGF) receptor daf-2 (FIG. 5*g-i*), which was used for gene mapping and identification. The pv17 allele introduces a single amino acid substitution (G46D) resulting in a reduction of function phenotype. The curated sequence slightly differs from the one published (FIG. 6).

sul-2 Encodes a Sulfatase of Steroid Hormones

Figure 7:
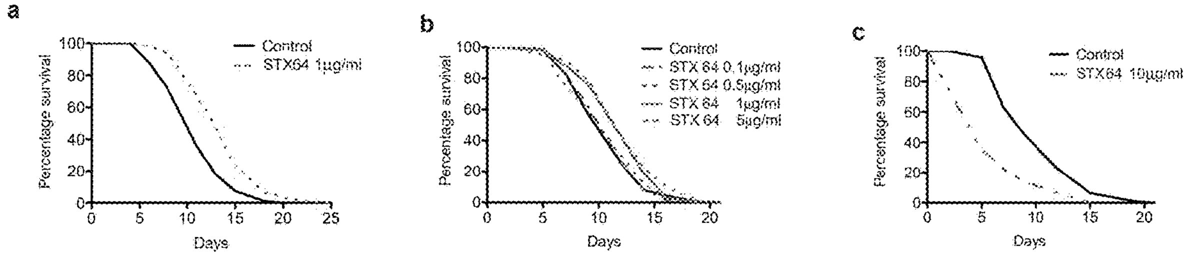
FIGS. 7*a*-7*d* Treatment with STX64 phenocopies longevity and genetic interaction of sul-2 mutants.
Figure 7:
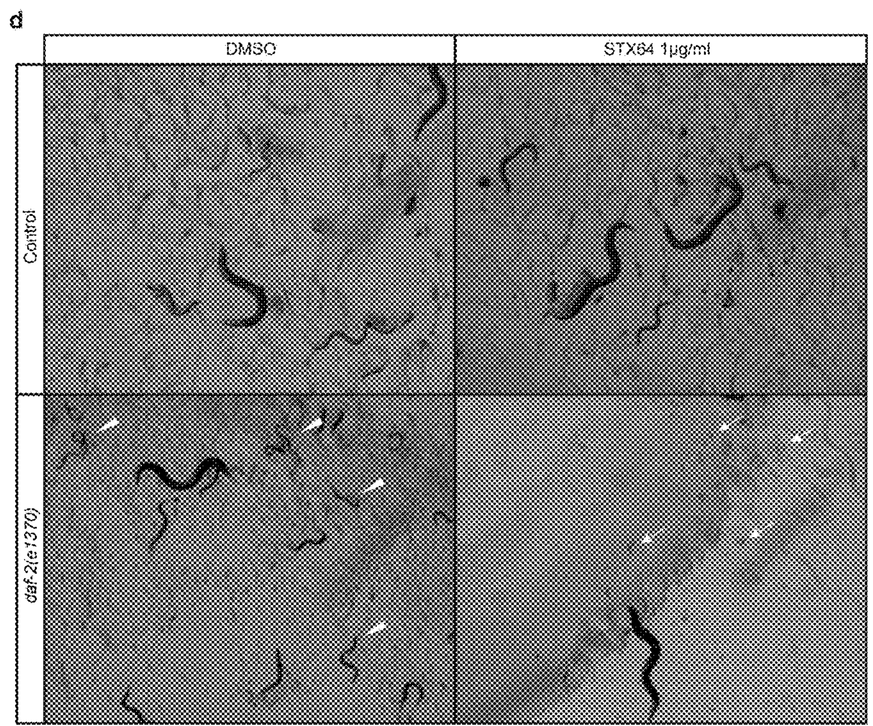

Sulfatases are a large protein family involved in different biological processes and with a wide range of substrates. The placement of curated sul-2 in the sulfatases phylogenetic tree is uncertain, but when compared to mammalian sulfatases, sul-2 clusters closer to the Arylsulfatases type H, F, E, D and the steroid sulfatase type C (FIG. 1*c*) which probably originated from a common ancestor gene. sul-1 and sul-3 belong to a different family of sulfatases (FIG. 1*c*). We hypothesized that sul-2 may exert its activity by modifying sulfated steroid hormones. Steroid hormone sulfatases are conserved proteins that participate, among other processes, stimulating proliferation in hormone-depending cancers. Specific inhibitors for this type of enzymes have been generated, such as STX6410, which has been used to treat patients with hormone-depending cancers. We treated wild type animals with STX64 and observed an increase in longevity (FIG. 1*d* and FIG. 7*a-c*). STX64 treatment also phenocopies other sul-2 mutant phenotypes (FIG. 7*d*). STX64 does not further increase the longevity of sul-2 deletion mutants, suggesting STX64 increases longevity is by inhibiting the sulfatase activity of SUL-2 (FIG. 1*d*).

Figure 2:
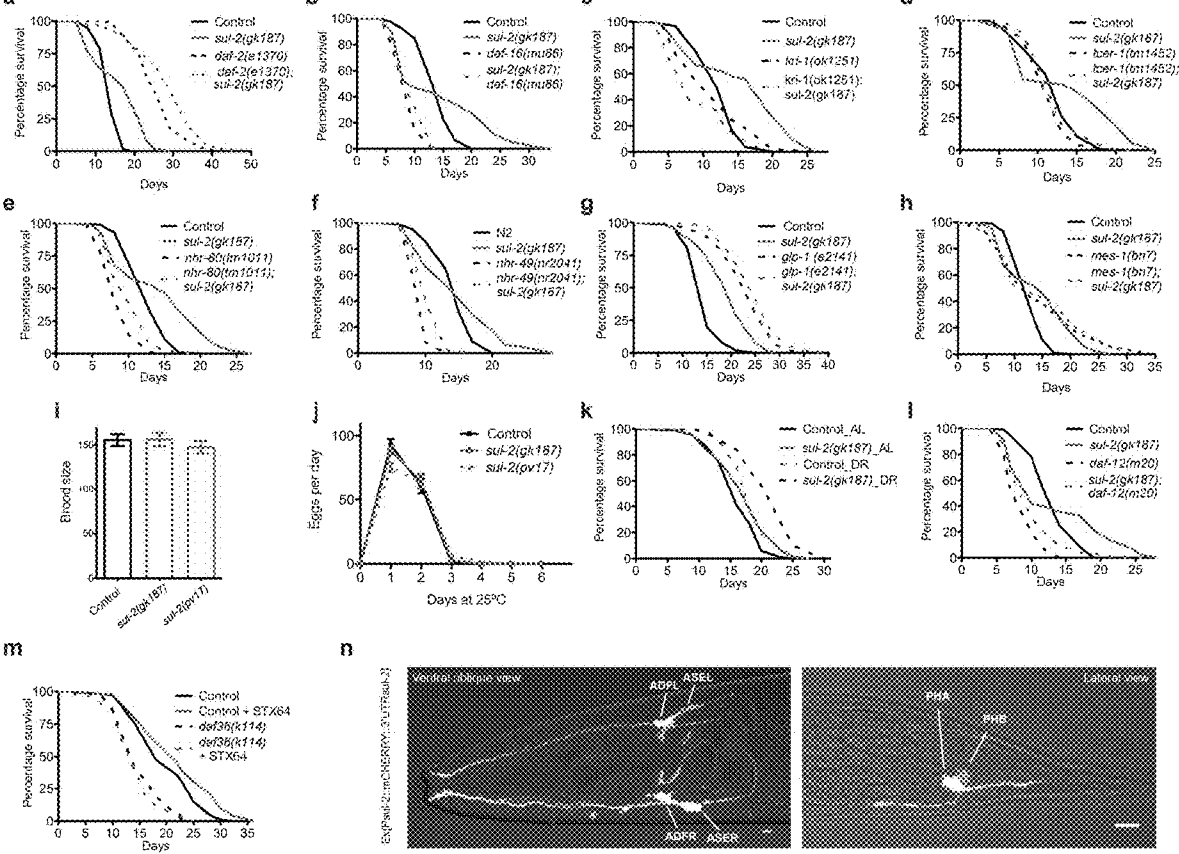
FIGS. 2*a*-2*n* illustrate genetic interactions and cellular location of sul-2 expression. Genetic analysis shows that sul-2 mimics most of the genetic interaction described for animals without germline, but do not affect fertility. a sul-2 enhances longevity in daf-2(e1370) background.
FIG. 2*b* illustrates that daf-16 transcription factor is required for sul-2 longevity.
FIGS. 2*c*, 2*d*, and 2*e* illustrate that the essential factors for germline-loss longevity kri-1(ok1251), tcer-1(tm1452), and partially nhr-80(tm1011) are required for sul-2 longevity.
FIG. 2*f* illustrates that nhr-49(nr2041) does not suppress sul-2 increased lifespan.
FIGS. 2*g* and 2*h* illustrate that sul-2 deletion has not significant increase of longevity in germline-less mutants glp-1(e2141) and mes-1(bn7).
FIG. 2*i* illustrates that brood size of sul-2 mutants are not significant different to wild type. Mean±SEM; One-way ANOVA test; ns.
FIG. 2*j* illustrates that reproductive period of sul-2 mutants are not affected (25° C.).
FIG. 2*k* illustrates that dietary restriction conditions (DR) show enhanced longevity in sul-2 deletion background.
FIG. 2*l* illustrates that daf-12 transcription factor is required for sul-2 longevity.
FIG. 2*m* illustrates that the Rieske-like oxygenase daf-36 is necessary for the increase of longevity upon inhibition of steroid hormone sulfatase, STX64 (1 μg/ml).
Figure 8:
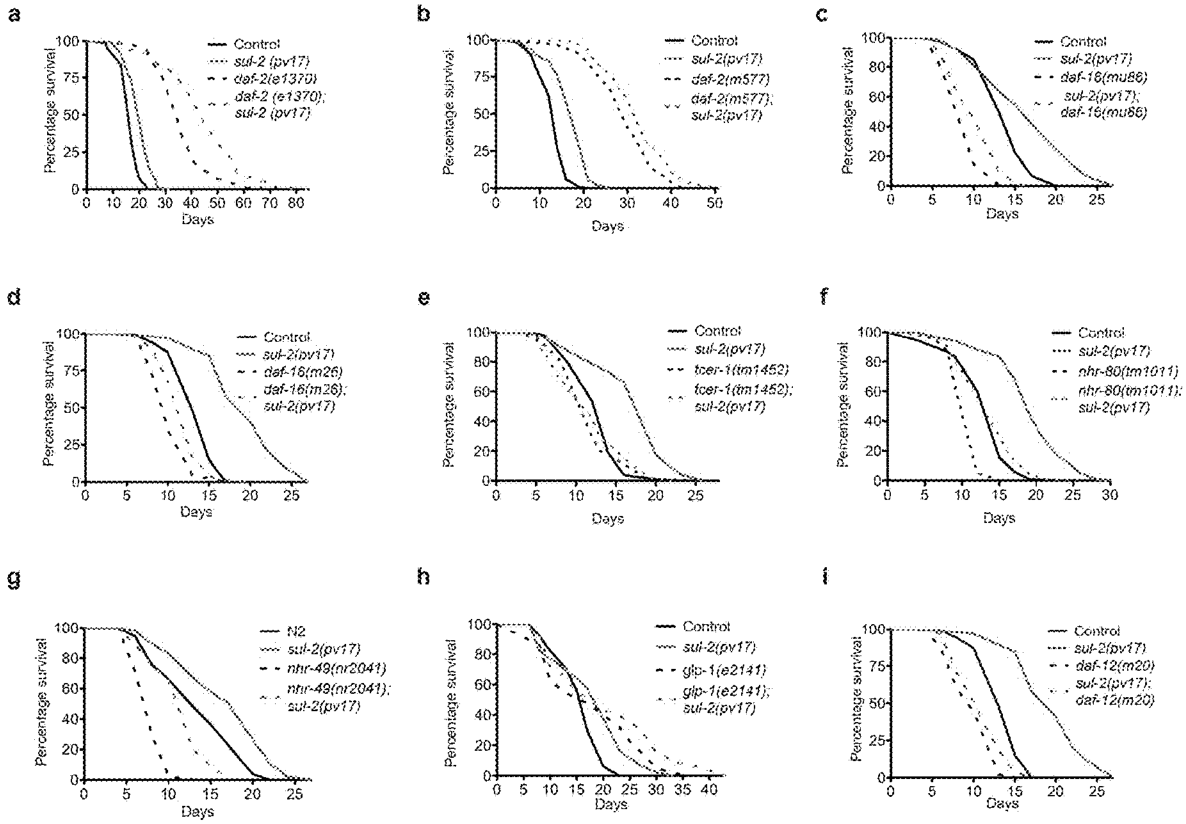
FIGS. 8*a*-8*i* illustrate that genetic interactions of sul-2 (pv17) allele. sul-2-point mutation allele pv17 shows similar phenotypes in longevity interactions assayed as sul-2 deletion, except in glp-1 background.
Figure 9:
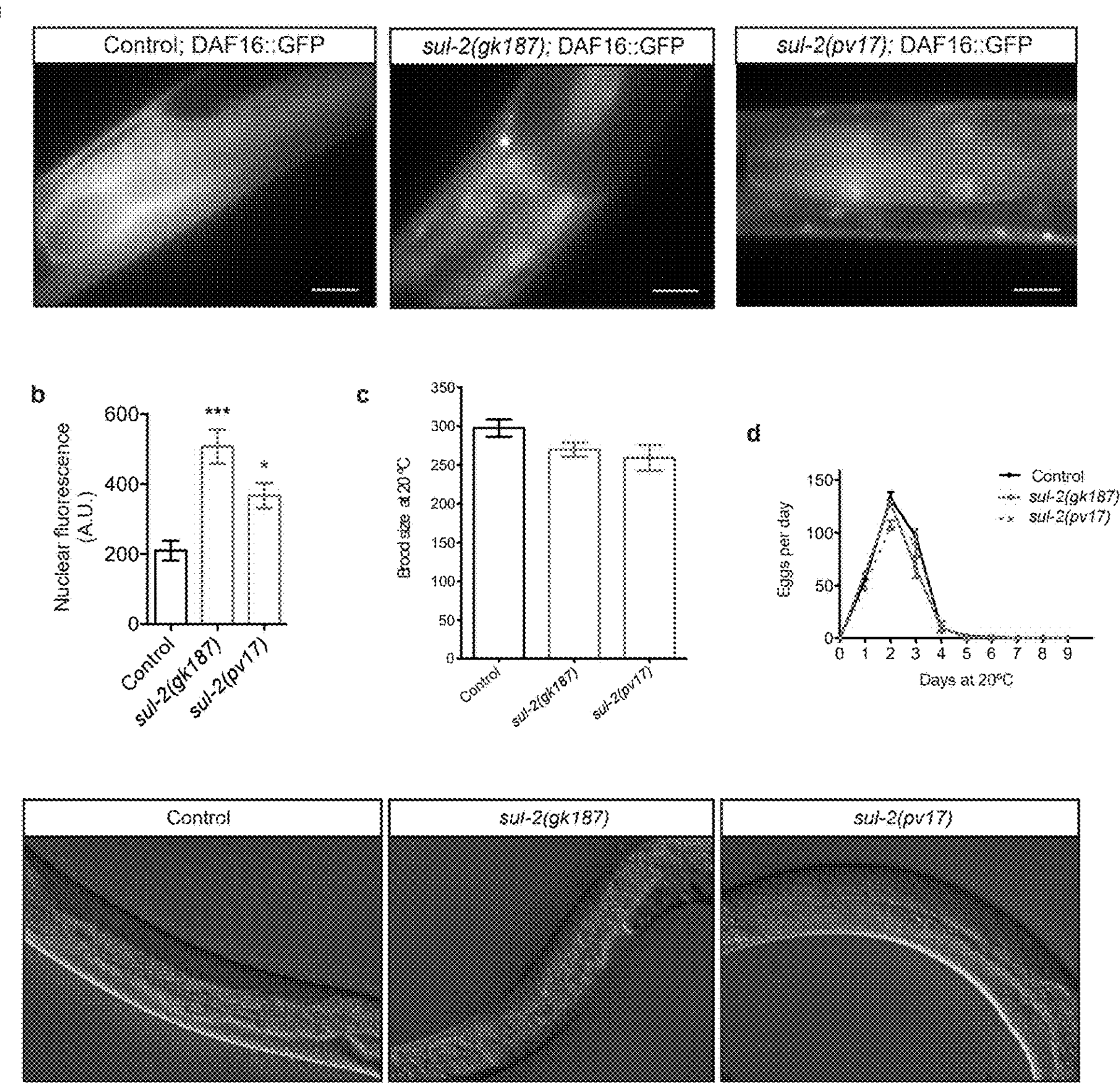
FIGS. 9*a*-9*e* show that sul-2 mutants affect DAF-16 location in intestinal cells, but they do not affect reproduction or gonad morphology.
Figure 10:
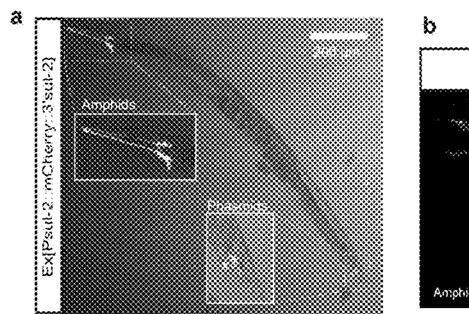
FIGS. 10*a*-10*d* show that sul-2 is expressed in amphid and phasmid sensory neurons. Extrachromosomal transgenic worms express mCherry under sul-2 promoter and its 3'UTR only in few sensory neurons.
Figure 10:
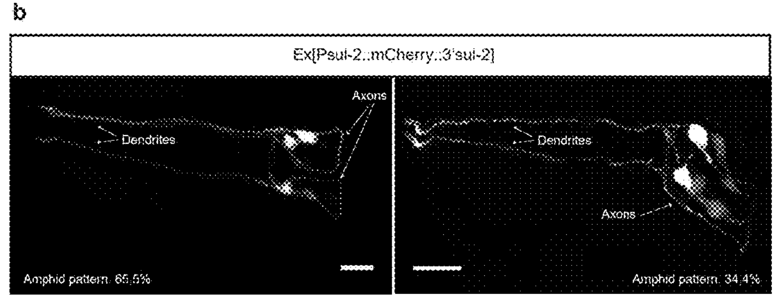
Figure 10:
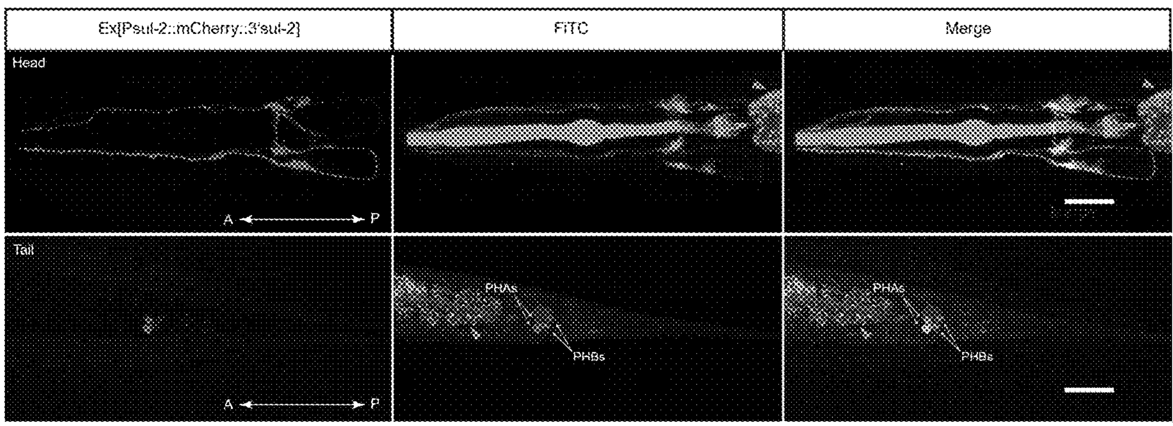
Figure 10:
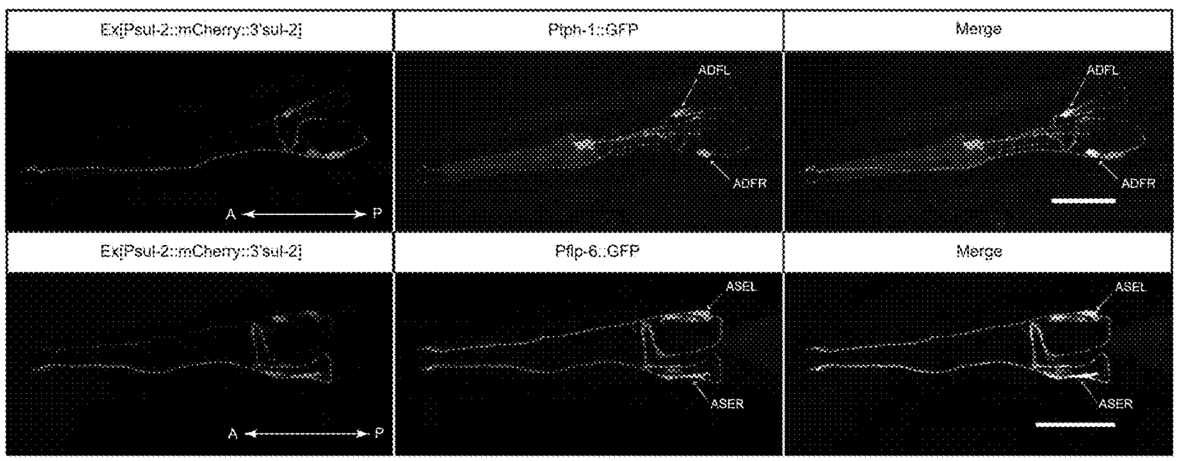

We measured sulfated steroid hormones levels by a high-resolution HPLC-TOF-MS in sul-2 mutant and found a higher proportion of sulfated hormones in this strain as compared to wild type worms (FIG. 1*e*). All these data suggest that SUL-2 can act as a steroid hormones sulfatase and regulates longevity through the alteration of the sulfated state of one or several steroid hormones. The increased longevity of sul-2 depends on genes mediating gonadal longevity To investigate if sul-2 acts in a known longevity pathway, we performed genetic interaction studies with known alleles that affect longevity. Mutations in the IGF receptor daf-2 increase lifespan through the transcription factor DAF-16/FOXO12. sul-2 mutations further extend the lifespan of daf-2 reduction of function mutants (FIG. 2*a* FIG. 8*a-b*), suggesting that sul-2 acts in a different pathway to regulate longevity. However, the increased longevity of sul-2 mutants is mainly suppressed by DAF-16 loss-of-function (FIG. 2*b* and FIG. 8*c-d*). Longevity conferred by lack of germline also requires DAF-1612, 13, which translocates to the nuclei mainly in intestinal cells. However, in insulin signaling mutants, DAF-16 localizes to the nucleus of most cells. In sul-2 mutants, DAF-16 localizes predominantly to intestinal nuclei (FIG. 9*a-b*), suggesting a role for sul-2 in germline mediated longevity. Other essential factors for germline-mediated longevity, such as the intestinal ankyrin-repeat protein KRI-1/KRIT-1 and the transcription elongation factor TCER-1/TCERG1 are also required for a fully increased longevity of sul-2 mutants, although a mild effect is observed with the nuclear hormone receptor NHR-80 and no effect was observed in NHR-49, which are also required for germline-mediated longevity (FIG. 2*c-f* and FIG. 8*e-g*). Moreover, deletion of sul-2 has little effect on the longevity of the germline-less mutant glp-1 or mes-1 longevity18 (FIG. 2*g-h*); However, we do observe an additive effect in the reduction of function allele pv17 in a glp-1 background (FIG. 8*h*), which may suggest some additional effect of the mutated protein.

All these data suggest that sul-2 mediates signaling from the gonad to regulate longevity. Interestingly, sul-2 mutations do not affect fertility, reproductive age or gonad morphology (FIG. 2*i-j* and FIG. 9*c-e*). Taken together, our findings suggest that sul-2 affects a signal that regulates longevity to adjust lifespan to the reproductive status without affecting gonadal function. Similar to germline ablation, we also observed that sul-2 mutants increase further the longevity in dietary restriction suggesting that sul-2 is not implied in this intervention that affects longevity (FIG. 2*k*). In germline-less animals, the activation of the nuclear receptor DAF-12 by bile acid-like steroids called dafachronic acids (DAs) triggers an increase in longevity 20. We observed that daf-12 is also needed for the increased longevity of sul-2 mutants (FIG. 2*l* and FIG. 8*i*), indicating that sul-2 inactivation causes the alteration of the sulfated steroid hormones pool, generating a signal upstream of DAF-12 that imitates the longevity signals of gonad depleted animals. DAF-36 converts cholesterol to 7-dehydrocholesterol in the first step of the biosynthetic pathway of Δ7-DA21, 22. Therefore, DAF-36 is also needed for the increased longevity of germline-less animals23. Similarly, DAF-36 is required for the longevity conferred by the steroid sulfatase inhibitor STX64 (FIG. 2*m*) placing the signal generated by sulfated steroid hormones upstream of or parallel to the biosynthesis of DAs.

sul-2 is Expressed in Sensory Neurons

Figure 11:
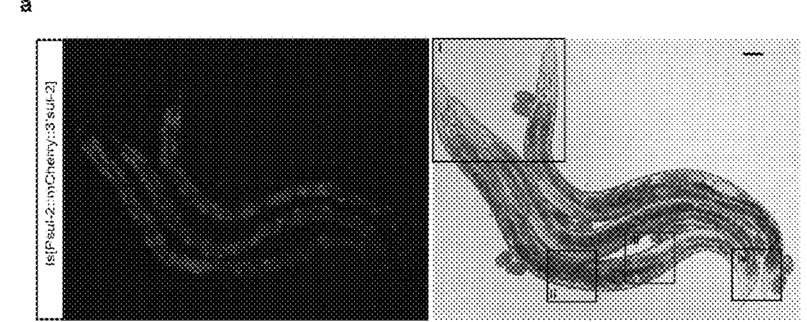
FIGS. 11*a*-11*e* show that sul-2 is not expressed in gonadal tissues and is not affected in neuronal functions.
Figure 11:
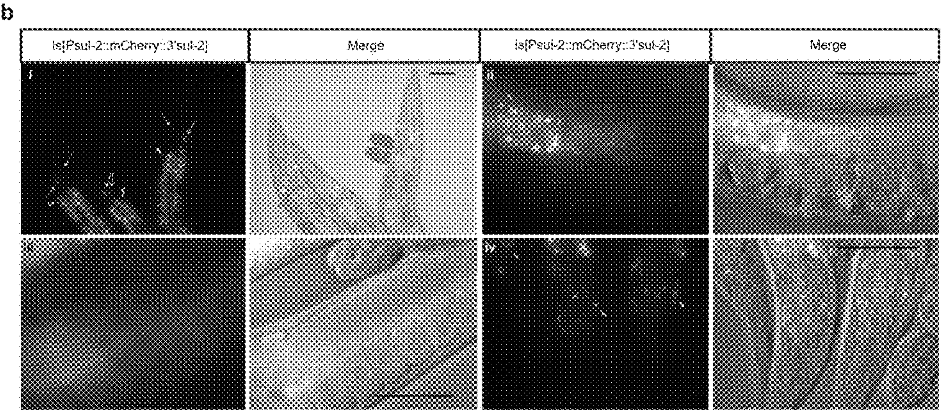
Figure 11:
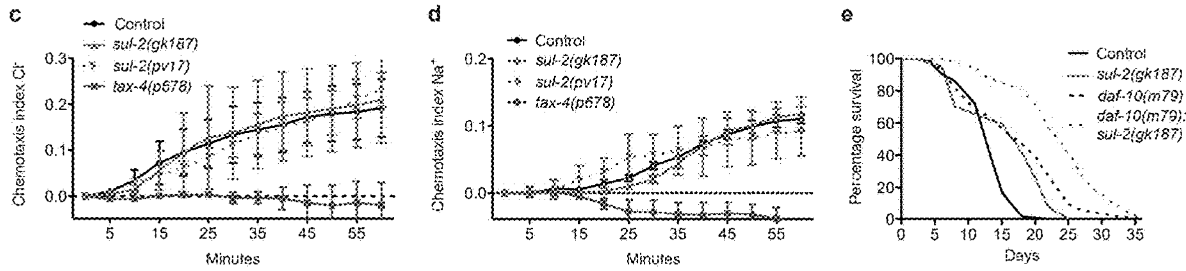

We have studied the anatomical location of sul-2 expression from an extrachromosomal array and in single-copy insertion transgenic strains. We found that sul-2 is expressed only in a few sensory neurons, mainly in the amphids ADF and ASE, and phasmids PHA and PHB. There is no detectable expression in the germline in any transgenic strains (FIG. 2*n* and FIG. 10, 11*a-b*). ASE neurons are responsible for the attractive response of Na+ and Cl−, among others. Defects in odor sensing affect longevity. Therefore, we tested the ability of sul-2 mutants to respond to Cl− or Na+ and found no differences compared to wild type animals (FIG. 11*c-d*). Furthermore, sul-2 mutation increases the longevity of daf-10(m79), a long-lived mutant defective in sensory cilia formation25 (FIG. 11*e*). These results show that the longevity phenotype observed in sul-2 mutants is not due to the impaired functionality of sensory neurons. Reduction of sul-2 improves aging associated diseases in *C. elegans* Aging is considered the main risk factor for the onset of neurodegenerative disorders like Parkinson, Huntington, or Alzheimer's diseases. These disorders are caused by the progressive decline of proteostasis, which results in protein aggregation that compromises cellular functions and finally causes cell death. Germline-deficient *C. elegans* delay the symptoms derived from the proteotoxicity of ectopically expressed human β-amyloid (βA). We tested if sul-2 mutations or STX64 treatment improves the symptoms of *C. elegans* models for neurodegenerative diseases. In a *C. elegans* Parkinson's disease model, in which human α-synuclein expression in muscle cells causes age-dependent paralysis, sul-2 mutation or treatment with STX64 significantly improved mobility (FIG. 3*a-b*, FIG. 12*a-c*).

Figure 3:
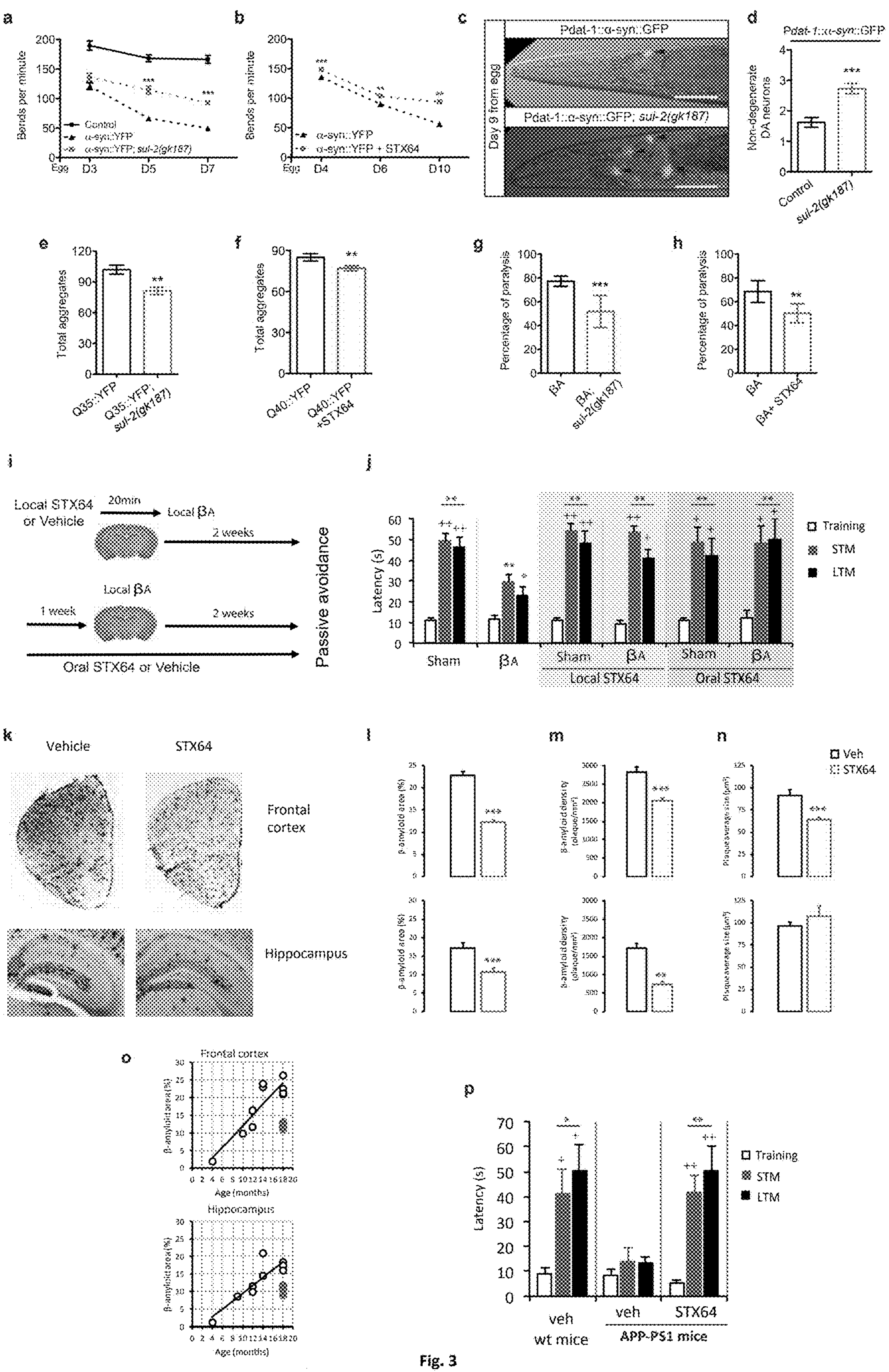
FIGS. 3*a*-3*p* illustrate reduction of steroid hormone sulfatase activity ameliorates the symptoms of proteotoxicity models in *C. elegans* and murine model.
FIG. 3*b* illustrates that NL5901 strain expressing α-synuclein in muscle cells reduce mobility with age under treatment with STX64 (1 μg/ml) ((n≥9 per day). Additional biological replicates assays are shown in FIGS. 12 *a* and *c*.
FIGS. 3*c* and 3*d* illustrate that neurodegeneration of dopaminergic (DA) neurons in UA44 strain expressing human α-synuclein is reduced in sul-2(gk187) background. A representative image of each condition and quantification of survivor neurons at day 9. Scale 50 μm. Data from two biological replicates are displayed, n=37.
FIG. 3*e* illustrates that Q35 aggregates are reduced in sul-2(gk187) background (n≥6), 8-day old worms.
FIG. 3*f* illustrates that Q40 aggregates are reduced by treatment with STX64 (1 μg/ml) in Q40 background (n≥12), 5-day old worms. Strains AM140 and AM141 respectively.
FIG. 3*g* illustrates that expression of human β-amyloid in muscle provokes a thermodependent paralysis in L4-young adult stage in GMC101 strain, the paralysis phenotype is ameliorated in sul-2 deletion mutant. Data display from four independent biological replicates, n=125.
FIG. 3*h* illustrates that expression of human β-amyloid in muscle provokes a thermodependent paralysis in L4-young adult stage in GMC101 strain, the paralysis phenotype is ameliorated by STX64 (1 μg/ml) treatment. Data display from six independent biological replicates, n≥215.
FIGS. 3*i* and 3*j* illustrate that the effect of intrahippocampal and oral administration of STX64 in the passive avoidance test in wild type mice injected with β-amyloid oligomers in the hippocampus. The number of mice in each group were >5.
FIG. 3*k* illustrates that representative β-amyloid-immunoreactive images assessed in the frontal cortex and the hippocampus of APP-PS1 mice older than 15 months of age after 3-4 weeks of vehicle or STX64 intake (0.005 mg/ml in drink water).
FIGS. 3*l*-3*n* illustrate quantification of percentage of β-amyloid area (c), deposition density (d) and average plaque size (e) in the frontal cortex and the hippocampus of >15 months-old APP-PS1 mice after 3-4 weeks of oral administration with STX64 or vehicle. n=4 mice per groups.
FIG. 3*o* illustrates temporal course of β-amyloid deposition in APP-PS1 mice and the effect of 3-4 weeks STX64 oral treatment on β-amyloid area in the frontal cortex (upper panel) and the hippocampus (lower panel). The number of microphotographs used was more than 3 in all the mice used.
Figure 12:
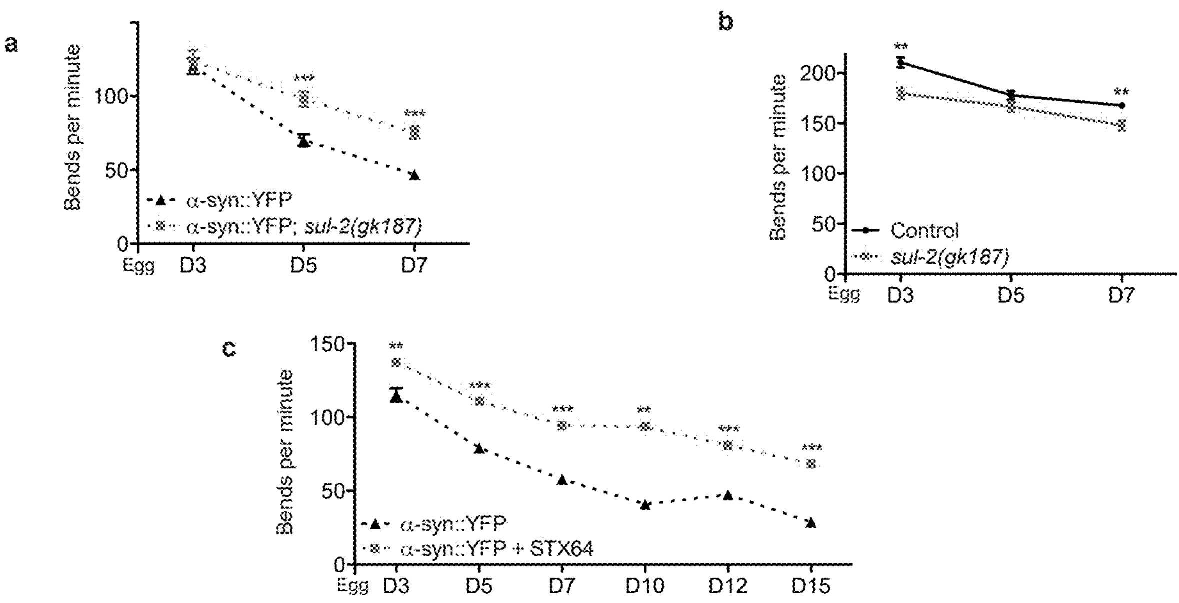
FIGS. 12*a*-12*g* illustrate that neurodegeneration phenotypes are ameliorated during aging when steroid sulfatase function is reduced, and α-synuclein aggregation decreases.
Figure 12:
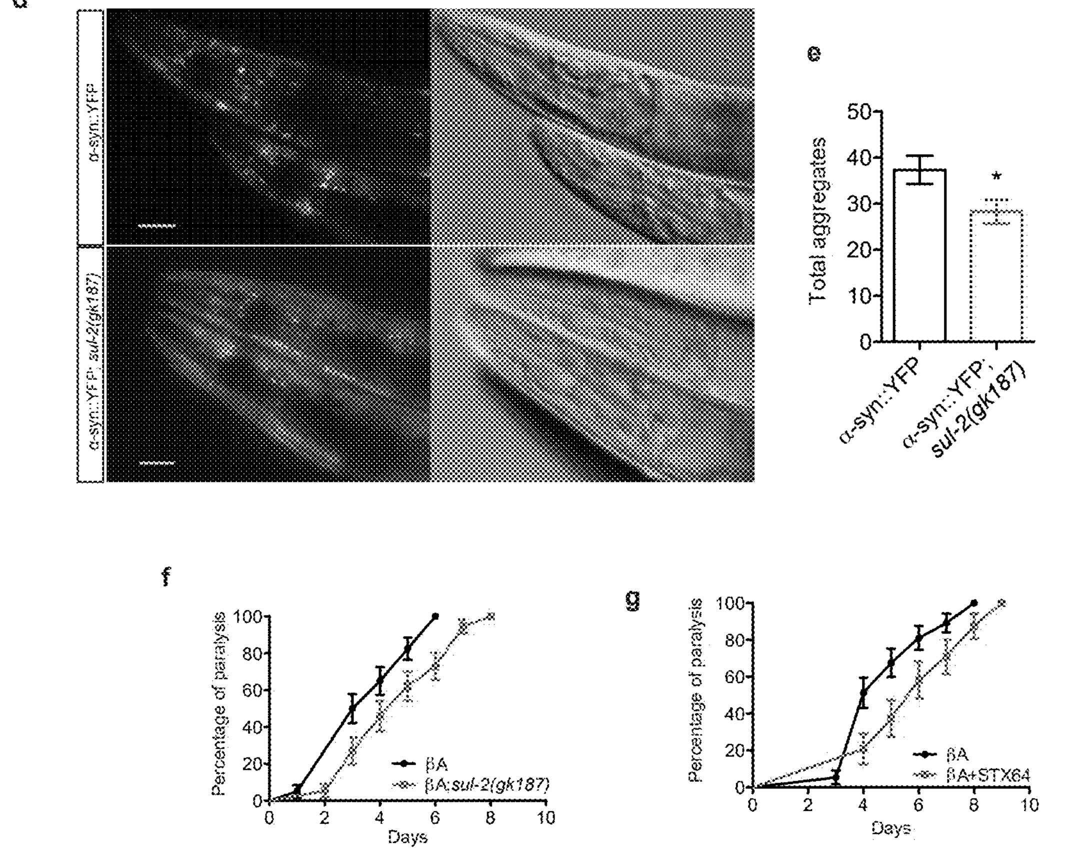

Loss of function of SUL-2 decreased the number of α-synuclein aggregates (FIG. 12*d-e*), suggesting better handling of protein aggregates in worms with reduced steroid sulfatase activity. To further assay the neuroprotective effect of reduced sul-2 activity, we tested a strain expressing α-synuclein in dopaminergic neurons. In this model, GFP-labelled dopaminergic neurons die due to α-synuclein toxicity. Consistently, sul-2 mutants showed increased neuron survival compared with control worms, indicating a neuroprotective action of reduced steroid-hormone sulfatase activity (FIG. 3*c-d*). In a Huntington neurodegenerative model expressing polyglutamine repeats fused to YFP, a construct that aggregates in adult worms, we found that both sul-2 mutation and treatment with STX64 reduced the number of aggregates (FIG. 3*e-f*). We also tested two different strains of Alzheimer's disease (AD) in worms, where immobility is caused by expression of βA protein in muscle cells. Consistently, sul-2 mutation and STX64 treatment delayed paralysis (FIG. 3*g-h* and FIG. 12*fg*). All these data show that inhibition of sul-2 protects the nematode against aging related proteotoxicity.

Reduction of Activity of sul-2 Improves Alzheimer in a Mammal Model

As STX64 ameliorated neurodegeneration in *C. elegans* models, we tested the effect of this drug on cognitive alterations provoked by intrahippocampal βA oligomers infusion, an acute AD mammalian model (FIG. 3*i*). Previously, it has been reported that local administration of DU-14, an inhibitor of steroid hormones sulfatase, could alleviate memory loss caused by intrahippocampal administration of βA oligomers in a mammalian model. We observed that both, local and systemic STX64 treatments reverted the cognitive deficiencies, measured by passive avoidance test, caused by intrahippocampal administration of βA oligomers (FIG. 3*j*). To evaluate the effect of STX64 oral treatment on amyloid pathology in a chronic AD mice model, we assessed the effect of 3-4 weeks of STX64 oral treatment on amyloid deposition in the neocortex (the cerebral cortex and the hippocampus) of >15-month-old APP-PS1 mice (FIG. 4*k*). At this age corresponding to a late stage of amyloid deposition in the neocortex of the APP218 PS1 model, the analysis of βA plaque density and size revealed a significant reduction, except for plaque size in the hippocampus, in mice treated with STX64. Moreover, βA immunoreactive area is reduced in both tissues (FIG. 4*k-n*). Interesting, when we compared βA deposition in old (>15-month-old) APP-PS1 mice treated with STX64 with the normal temporal course of amyloid deposition in un-treated APP-PS1 mice, we observed that STX64 reduces βA deposition in APP-PS1 mice older than 15 month compared to that observed in APP-PS1 mice of 10-12 months of age (FIG. 4*o*). All these results indicate that STX64 treatment in APP-PS1 mice reduces βA deposition. We wondered if this histological improvement correlated with amelioration of cognitive behavioral deficit. For that, we compared cognition capacities in APP-PS1 mice older than 15-month-old treated with vehicle or STX64 for 3-4 weeks. While vehicle-treated APP-PS1 mice showed a deficit in passive avoidance test (FIG. 4*p*), those mice treated with STX64 completely reverted cognitive deficiencies, reaching similar levels to <15-month-old wild type mice. All these results point out that the alterations in βA metabolism provoked by STX64 reduce the cognitive behavior deficiencies induced by βA accumulation in acute and chronic AD mice models, suggesting a potential for STX64 as a pharmacological therapy against neurodegenerative diseases.

Sulfated C19 Androgens Hormones Recapitulate the Beneficial Effect of Reduction of sul-2 Activity In mammals, sulfated hormones have been long considered inactive forms that function mainly as reservoirs and are activated by steroid sulfatases6, although a direct action of sulfated hormones in the reproductive and the nervous system has been observed. In this last tissue, those hormones are named neurosteroids and their main function is the modulation of neurotransmition. In order to sort out whether the beneficial effect of sul-2 inhibition is due to the reduction of non-sulfated hormones or the increase of sulfated hormones, we tested the commercially available sulfated steroid hormones that are highly presented in the mutant (Table 1). We observed that the C19 androgens dehydroepiandrosterone sulfate (DHEAS), testosterone sulfate (TS) and epitestosterone sulfate (ES) improved the mobility in the Parkinson model of *C. elegans*, with a better result for ES (FIG. 4*a*). Similar results are obtained in the Alzheimer model with TS and ES but not with DHEAS (FIG. 4*b* and FIG. 13*a*). Non-sulfated DHEA or non-sulfated testosterone showed no effect, neither pregnenolone sulfate, which belongs to the C21 group of steroid hormones (FIG. 4*c-d*). These results indicate that at least some sulfated C19 androgens are involved in the protective effect against protein aggregation diseases and strongly suggest that the beneficial effect of sul-2 inhibition is due to the increased levels of this type of hormones. In agreement with these results, treatment with the antiandrogenic compound abiraterone (Abi)36, did not affect wild type animals but suppressed the beneficial effect of sul-2 mutation (FIG. 4*e*).

We then tested if those hormones are also involved in the other phenotypes observed in the sul-2 mutant. Treatment with any of those sulfated hormones generated an increase of L1 arrest in a daf-2(e1370) background as observed in sul-2 or STX 64 treated animals (FIG. 13*b*). Interestingly, treatment with ES, but not TS or DHEAS, increased in longevity on a wild type background and did not further increase longevity in sul-2 mutants backgrounds (FIG. 4*f-g* and FIG. 13*c-d*), indicating that both interventions share the same molecular mechanism. Thus, addition of ES recapitulated all the phenotypes described for sul-2 inhibition and strongly suggesting that the causative effect of sul-2 mutation is due to the increase of C19 androgen sulphated mhormones related to ES.

The invention claimed is:

1. A method for the treatment of proteotoxicity in a protein-aggregation disease in a subject, wherein the protein-aggregation disease is Alzheimer's disease or Parkinson's disease, comprising administering a composition comprising sulfated C19 androgens selected from the group consisting of testosterone sulfate (TS), or any salts or esters thereof, and epitestosterone sulfate (ES), or any salts or esters thereof, to the subject.

2. A method for slowing down the progression of a protein-aggregation disease by inhibiting the formation of protein aggregates and/or delaying the onset of the protein-aggregation disease by inhibiting the formation of protein aggregates, wherein the protein-aggregation disease is Alzheimer's disease, or Parkinson's disease, comprising administering a composition comprising sulfated C19 androgens selected from the group consisting of testosterone sulfate (TS), or any salts or esters thereof, and epitestosterone sulfate (ES), or any salts or esters thereof, to the subject.

3. The method according to claim 1, wherein the composition is simultaneously or subsequently administered with a sulfatase inhibitor selected from the group consisting of 2-(hydroxyphenyl) indol sulfate, 5-androstene-3β, DU-14 (CAS NO: 186303-55-9), COUMATE (4-methylcoumarin-7-O-sulphamate), EMATE (CAS Number: 148672-09-7), and the sulfatase inhibitor of Formula (I):

(I)

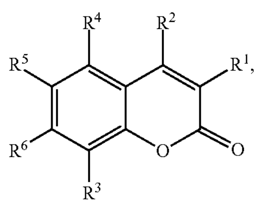

wherein:

R1-R6 are independently selected from hydrogen, halogen, hydroxyl, sulfamate, alkyl and salts thereof;

at least one of R1-R6 is a sulfamate group; and two or more of R1-R6 are linked together to form an additional cyclic structure.

4. The method according to claim 3, wherein the sulfatase inhibitor is compound STX64 of Formula (II):

(II)

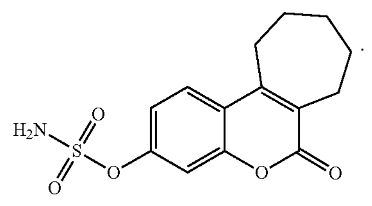

or any salts thereof.

5. The method according to claim 1, wherein the composition is a pharmaceutical composition comprising the C19 androgens and optionally a pharmaceutically acceptable carrier and/or diluent.

6. The method according to claim 1, wherein the composition is a nutraceutical composition.

7. The method according to claim 1, wherein the composition is a dietary supplement.

8. The method according to claim 1, wherein the composition is administered orally.

9. The method according to claim 2, wherein the composition is simultaneously or subsequently administered with a sulfatase inhibitor selected from the group consisting of 2-(hydroxyphenyl) indol sulfate, 5-androstene-3β, DU-14 (CAS NO: 186303-55-9), COUMATE (4-methylcoumarin- 7-O-sulphamate), EMATE (CAS Number: 148672-09-7), and the sulfatase inhibitor of Formula (I):

(I)

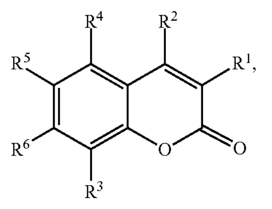

wherein:

R1-R6 are independently selected from hydrogen, halogen, hydroxyl, sulfamate, alkyl and salts thereof;

at least one of R1-R6 is a sulfamate group; and two or more of R1-R6 are linked together to form an additional cyclic structure.

10. The method according to claim 9, wherein the sulfatase inhibitor is compound STX64 of Formula (II):

(II)

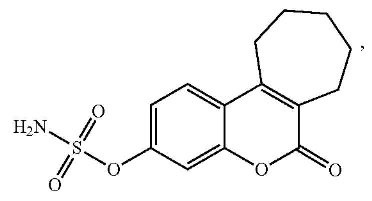

or any salts thereof.

11. The method according to claim 2, wherein the composition is a pharmaceutical composition comprising the C19 androgens and optionally a pharmaceutically acceptable carrier and/or diluent.

12. The method according to claim 2, wherein the composition is a nutraceutical composition.

13. The method according to claim 2, wherein the composition is a dietary supplement.

14. The method according to claim 2, wherein the composition is administered orally.

* * * * *